(12) United States Patent
Inoue et al.

(10) Patent No.: US 8,470,032 B2
(45) Date of Patent: Jun. 25, 2013

(54) INTRAOCULAR LENS INSERTION DEVICE

(75) Inventors: Masanobu Inoue, Honjo (JP); Noriyuki Shoji, Kitamoto (JP)

(73) Assignee: Hoya Corporation, Tokyo (JP)

( * ) Notice: Subject to any disclaimer, the term of this patent is extended or adjusted under 35 U.S.C. 154(b) by 0 days.

(21) Appl. No.: 13/061,143

(22) PCT Filed: Aug. 27, 2009

(86) PCT No.: PCT/JP2009/064976
§ 371 (c)(1),
(2), (4) Date: Mar. 17, 2011

(87) PCT Pub. No.: WO2010/026919
PCT Pub. Date: Mar. 11, 2010

(65) Prior Publication Data
US 2011/0264101 A1    Oct. 27, 2011

(30) Foreign Application Priority Data
Sep. 4, 2008   (JP) ................................ 2008-227641

(51) Int. Cl.
*A61F 9/00*    (2006.01)

(52) U.S. Cl.
USPC ........................................ 623/6.12; 606/107

(58) Field of Classification Search
USPC ........................................ 606/107; 623/6.12
See application file for complete search history.

(56) References Cited

U.S. PATENT DOCUMENTS

| 2,761,446 A | 9/1956 | Reed |
| 4,205,747 A | 6/1980 | Gilliam et al. |
| 4,269,307 A | 5/1981 | LaHaye |
| 4,423,809 A | 1/1984 | Mazzocco |
| 4,573,998 A | 3/1986 | Mazzocco |
| 4,608,049 A | 8/1986 | Kelman |
| 4,634,423 A | 1/1987 | Bailey |
| 4,681,102 A | 7/1987 | Bartell |
| 4,697,697 A | 10/1987 | Graham et al. |
| 4,699,140 A | 10/1987 | Holmes |

(Continued)

FOREIGN PATENT DOCUMENTS

| DE | 3610925 | 10/1987 |
| DE | 4110278 | 10/1992 |

(Continued)

OTHER PUBLICATIONS

PCT International Search Report dated Sep. 29, 2009 for PCT App. Ser. No. PCT/JP09/64976.

*Primary Examiner* — Kathleen Holwerda
(74) *Attorney, Agent, or Firm* — Henricks, Slavin & Holmes LLP

(57) ABSTRACT

There is provided an intraocular lens insertion device capable of more easily inserting an intraocular lens into an eye. An intraocular lens insertion device 1 comprises a main body 2, an operation portion 5 and a cartridge 4 attached to the main body 2. The operation portion 5 has a plunger 6 integrally provided thereon and serving as a transmitting member, and a rod 7 provided on a distal end of the plunger 6 and serving to push out the intraocular lens. The intraocular lens insertion device 1 further comprises a restraint portion 10, and thus allows the rod 7 to first push an intraocular lens 8 by a predetermined distance and then be temporarily stopped before the intraocular lens 8 is released from the cartridge 4 toward the outside.

16 Claims, 12 Drawing Sheets

U.S. PATENT DOCUMENTS

| | | |
|---|---|---|
| 4,702,244 A | 10/1987 | Mazzocco |
| 4,715,373 A * | 12/1987 | Mazzocco et al. ............ 606/107 |
| 4,747,404 A | 5/1988 | Jampel et al. |
| 4,750,498 A | 6/1988 | Graham |
| 4,759,359 A | 7/1988 | Willis et al. |
| 4,763,650 A | 8/1988 | Hauser |
| 4,765,329 A | 8/1988 | Cumming et al. |
| 4,769,034 A | 9/1988 | Poley |
| 4,781,719 A | 11/1988 | Kelman |
| 4,787,904 A | 11/1988 | Severin |
| 4,819,631 A | 4/1989 | Poley |
| 4,834,094 A | 5/1989 | Patton |
| 4,836,201 A | 6/1989 | Patton |
| 4,862,885 A | 9/1989 | Cumming |
| 4,880,000 A | 11/1989 | Holmes et al. |
| 4,919,130 A | 4/1990 | Stoy et al. |
| 4,934,363 A | 6/1990 | Smith et al. |
| 4,955,889 A | 9/1990 | Van Gent |
| 4,976,716 A | 12/1990 | Cumming |
| 4,988,352 A | 1/1991 | Poley |
| 4,994,028 A | 2/1991 | Leonard et al. |
| 5,066,297 A | 11/1991 | Cumming |
| 5,098,439 A | 3/1992 | Hill et al. |
| 5,123,905 A | 6/1992 | Kelman |
| 5,139,501 A | 8/1992 | Klaas |
| 5,171,241 A | 12/1992 | Buboltz et al. |
| 5,176,686 A | 1/1993 | Poley |
| 5,178,622 A * | 1/1993 | Lehner, II ................ 606/107 |
| 5,190,552 A * | 3/1993 | Kelman ................... 606/107 |
| 5,190,553 A | 3/1993 | Kanert et al. |
| 5,222,972 A | 6/1993 | Hill et al. |
| 5,242,450 A | 9/1993 | McDonald |
| 5,275,604 A | 1/1994 | Rheinish et al. |
| 5,281,227 A | 1/1994 | Sussman |
| 5,304,182 A | 4/1994 | Rheinish et al. |
| 5,354,333 A | 10/1994 | Kammann et al. |
| 5,395,378 A | 3/1995 | McDonald |
| 5,425,734 A | 6/1995 | Blake |
| 5,454,818 A | 10/1995 | Hambleton et al. |
| 5,468,246 A | 11/1995 | Blake |
| 5,474,562 A | 12/1995 | Orchowski et al. |
| 5,494,484 A | 2/1996 | Feingold |
| 5,496,328 A | 3/1996 | Nakajima et al. |
| 5,499,987 A | 3/1996 | Feingold |
| 5,562,676 A | 10/1996 | Brady et al. |
| 5,571,113 A | 11/1996 | McDonald |
| 5,578,042 A | 11/1996 | Cumming |
| 5,582,613 A | 12/1996 | Brady |
| 5,582,614 A | 12/1996 | Feingold |
| 5,584,304 A | 12/1996 | Brady |
| 5,616,148 A | 4/1997 | Eagles et al. |
| 5,620,450 A | 4/1997 | Eagles et al. |
| 5,643,275 A | 7/1997 | Blake |
| 5,643,276 A | 7/1997 | Zaleski |
| 5,653,715 A | 8/1997 | Reich et al. |
| 5,653,753 A | 8/1997 | Brady et al. |
| 5,702,402 A | 12/1997 | Brady |
| 5,702,441 A | 12/1997 | Zhou |
| 5,716,364 A | 2/1998 | Makker et al. |
| 5,728,102 A | 3/1998 | Feingold et al. |
| 5,735,858 A | 4/1998 | Makker et al. |
| 5,766,181 A | 6/1998 | Chambers et al. |
| 5,772,666 A | 6/1998 | Feingold |
| 5,772,667 A | 6/1998 | Blake |
| 5,776,138 A | 7/1998 | Vidal et al. |
| 5,800,442 A | 9/1998 | Wolf et al. |
| 5,803,925 A | 9/1998 | Yang et al. |
| 5,807,400 A | 9/1998 | Chambers et al. |
| 5,810,833 A | 9/1998 | Brady et al. |
| 5,810,834 A | 9/1998 | Heyman |
| 5,860,984 A | 1/1999 | Chambers et al. |
| 5,860,986 A | 1/1999 | Reich et al. |
| 5,868,751 A | 2/1999 | Feingold |
| 5,868,752 A | 2/1999 | Makker et al. |
| 5,873,879 A | 2/1999 | Figueroa et al. |
| 5,876,406 A | 3/1999 | Wolf et al. |
| 5,876,407 A | 3/1999 | Makker et al. |
| 5,876,440 A | 3/1999 | Feingold |
| 5,891,152 A | 4/1999 | Feingold |
| 5,902,307 A | 5/1999 | Feingold et al. |
| 5,919,197 A | 7/1999 | McDonald |
| 5,921,989 A | 7/1999 | Deacon et al. |
| 5,928,245 A | 7/1999 | Wolf et al. |
| 5,941,886 A | 8/1999 | Feingold |
| 5,942,277 A | 8/1999 | Makker et al. |
| 5,944,725 A | 8/1999 | Cicenas |
| 5,947,974 A | 9/1999 | Brady et al. |
| 5,947,975 A | 9/1999 | Kikuchi et al. |
| 5,957,748 A | 9/1999 | Ichiha |
| 6,001,107 A | 12/1999 | Feingold |
| 6,010,510 A | 1/2000 | Brown et al. |
| 6,022,358 A | 2/2000 | Wolf et al. |
| 6,048,348 A | 4/2000 | Chambers et al. |
| 6,051,000 A | 4/2000 | Heyman |
| 6,056,757 A | 5/2000 | Feingold et al. |
| 6,056,758 A | 5/2000 | Vidal et al. |
| 6,059,791 A | 5/2000 | Chambers |
| 6,074,397 A | 6/2000 | Chambers et al. |
| 6,083,230 A | 7/2000 | Makker et al. |
| 6,093,193 A | 7/2000 | Makker et al. |
| 6,129,733 A | 10/2000 | Brady et al. |
| 6,142,999 A | 11/2000 | Brady et al. |
| 6,143,000 A | 11/2000 | Feingold |
| 6,162,229 A | 12/2000 | Feingold et al. |
| 6,174,315 B1 | 1/2001 | Chambers et al. |
| 6,214,015 B1 | 4/2001 | Reich et al. |
| 6,241,737 B1 | 6/2001 | Feingold |
| 6,248,111 B1 | 6/2001 | Glick et al. |
| 6,251,114 B1 | 6/2001 | Farmer et al. |
| 6,254,607 B1 | 7/2001 | Makker et al. |
| 6,267,768 B1 | 7/2001 | Deacon |
| 6,283,975 B1 | 9/2001 | Glick et al. |
| 6,283,976 B1 | 9/2001 | Portney |
| 6,312,433 B1 | 11/2001 | Butts |
| 6,334,862 B1 | 1/2002 | Vidal et al. |
| 6,336,932 B1 | 1/2002 | Figueroa et al. |
| 6,355,046 B2 | 3/2002 | Kikuchi et al. |
| 6,371,960 B2 | 4/2002 | Heyman et al. |
| 6,386,357 B1 | 5/2002 | Egawa |
| 6,387,101 B1 | 5/2002 | Butts et al. |
| 6,398,788 B1 | 6/2002 | Makker et al. |
| 6,406,481 B2 | 6/2002 | Feingold et al. |
| 6,428,545 B2 | 8/2002 | Portney |
| 6,447,519 B1 | 9/2002 | Brady et al. |
| 6,447,520 B1 | 9/2002 | Ott et al. |
| 6,468,282 B2 | 10/2002 | Kikuchi et al. |
| 6,471,708 B2 | 10/2002 | Green |
| 6,491,697 B1 | 12/2002 | Clark et al. |
| 6,500,181 B1 | 12/2002 | Portney |
| 6,506,195 B2 | 1/2003 | Chambers et al. |
| 6,537,283 B2 | 3/2003 | Van Noy |
| 6,540,754 B2 | 4/2003 | Brady |
| 6,554,839 B2 | 4/2003 | Brady |
| 6,558,395 B2 | 5/2003 | Hjertman et al. |
| 6,607,537 B1 | 8/2003 | Binder |
| 6,629,979 B1 | 10/2003 | Feingold |
| 6,666,871 B2 | 12/2003 | Kikuchi et al. |
| 6,679,891 B2 | 1/2004 | Makker et al. |
| 6,685,740 B2 | 2/2004 | Figueroa et al. |
| 6,712,848 B1 | 3/2004 | Wolf et al. |
| 6,723,104 B2 | 4/2004 | Ott |
| 6,733,507 B2 | 5/2004 | McNicholas et al. |
| 6,858,033 B2 | 2/2005 | Kobayashi |
| 6,921,405 B2 | 7/2005 | Feingold et al. |
| 6,923,815 B2 | 8/2005 | Brady et al. |
| 7,014,641 B2 | 3/2006 | Kobayashi et al. |
| 7,025,782 B2 | 4/2006 | Kobayashi et al. |
| 7,033,366 B2 | 4/2006 | Brady |
| 7,037,312 B2 | 5/2006 | Kikuchi et al. |
| 7,074,227 B2 | 7/2006 | Portney |
| 7,097,649 B2 | 8/2006 | Meyer |
| 7,131,976 B2 | 11/2006 | Kobayashi et al. |
| 7,156,854 B2 | 1/2007 | Brown et al. |
| 7,348,038 B2 | 3/2008 | Makker et al. |
| 7,422,604 B2 | 9/2008 | Vaquero et al. |
| 7,429,263 B2 | 9/2008 | Vaquero et al. |
| 7,458,976 B2 | 12/2008 | Peterson et al. |

| | | | | | | |
|---|---|---|---|---|---|---|
| 7,476,230 | B2 | 1/2009 | Ohno et al. | JP | 5-103809 | 4/1993 |
| 7,494,505 | B2 | 2/2009 | Kappelhof et al. | JP | 8-024282 A | 1/1996 |
| 7,645,300 | B2 | 1/2010 | Tsai | JP | 8-505540 | 6/1996 |
| 2001/0007942 | A1 | 7/2001 | Kikuchi et al. | JP | 9-506285 A | 6/1997 |
| 2002/0103490 | A1 | 8/2002 | Brady | JP | 11-113939 A | 4/1999 |
| 2002/0151904 | A1 | 10/2002 | Feingold et al. | JP | 11-506357 A1 | 6/1999 |
| 2002/0165610 | A1 | 11/2002 | Waldock | JP | 2000-516487 A | 12/2000 |
| 2002/0193805 | A1 | 12/2002 | Ott et al. | JP | 2000-516488 A | 12/2000 |
| 2003/0040755 | A1 | 2/2003 | Meyer | JP | 2001-502563 | 2/2001 |
| 2003/0050647 | A1 | 3/2003 | Brady | JP | 2001-104347 A | 4/2001 |
| 2003/0139749 | A1 | 7/2003 | Kikuchi et al. | JP | 2002-516709 A | 6/2002 |
| 2003/0181921 | A1 | 9/2003 | Jeannin | JP | 2002-355268 A | 12/2002 |
| 2003/0195522 | A1 | 10/2003 | McNicholas | JP | 2002-541912 A | 12/2002 |
| 2003/0212406 | A1 | 11/2003 | Kobayashi et al. | JP | 2003-144480 A | 5/2003 |
| 2003/0212407 | A1 | 11/2003 | Kikuchi | JP | 3412106 B2 | 6/2003 |
| 2003/0212409 | A1 | 11/2003 | Kobayashi et al. | JP | 2003-210498 A | 7/2003 |
| 2004/0111094 | A1 | 6/2004 | Meyer | JP | 2003-325569 A | 11/2003 |
| 2004/0117012 | A1 | 6/2004 | Vincent | JP | 2003-325570 A | 11/2003 |
| 2004/0238392 | A1 | 12/2004 | Peterson et al. | JP | 2003-325572 A | 11/2003 |
| 2004/0243141 | A1 | 12/2004 | Brown | JP | 2004-024854 A | 1/2004 |
| 2005/0049606 | A1 | 3/2005 | Vaquero et al. | JP | 2004-188194 A | 7/2004 |
| 2005/0125000 | A1 | 6/2005 | Tourrette et al. | JP | 2004-351196 A1 | 12/2004 |
| 2005/0182419 | A1 | 8/2005 | Tsai | JP | 2006-181269 A | 7/2006 |
| 2005/0222578 | A1 | 10/2005 | Vaquero | JP | 2006-297146 A | 11/2006 |
| 2005/0261703 | A1 | 11/2005 | Feingold et al. | JP | 2006-333924 A | 12/2006 |
| 2006/0085013 | A1* | 4/2006 | Dusek et al. .................. 606/107 | JP | 2006-333981 A | 12/2006 |
| 2006/0167466 | A1 | 7/2006 | Dusek | JP | 2007-503872 A | 3/2007 |
| 2006/0293694 | A1 | 12/2006 | Futamura | JP | 2007-152010 A | 6/2007 |
| 2008/0033449 | A1 | 2/2008 | Cole et al. | JP | 2007-181604 A | 7/2007 |
| 2008/0058250 | A1 | 3/2008 | Cole et al. | JP | 2007-526091 A | 9/2007 |
| 2008/0086146 | A1 | 4/2008 | Ishii et al. | JP | 2008-521535 A | 6/2008 |
| 2008/0097459 | A1* | 4/2008 | Kammerlander et al. .... 606/107 | JP | 2008-212689 A | 9/2008 |
| 2008/0221584 | A1 | 9/2008 | Downer | WO | WO9407436 A1 | 4/1994 |
| 2009/0036898 | A1 | 2/2009 | Ichinohe | WO | WO9513022 A1 | 5/1995 |
| 2009/0043313 | A1 | 2/2009 | Ichinohe | WO | WO9628122 A1 | 9/1996 |
| 2009/0112223 | A1 | 4/2009 | Downer et al. | WO | WO9715253 A1 | 5/1997 |
| 2009/0204122 | A1 | 8/2009 | Ichinohe et al. | WO | WO9812969 A1 | 4/1998 |
| 2009/0216244 | A1 | 8/2009 | Pynson | WO | WO0045746 A1 | 8/2000 |
| 2009/0248031 | A1 | 10/2009 | Ichinohe | WO | WO0062712 A1 | 10/2000 |
| 2010/0161049 | A1 | 6/2010 | Inoue | WO | WO02071982 A1 | 9/2002 |
| 2010/0185206 | A1 | 7/2010 | Ichinohe et al. | WO | WO02096322 A1 | 12/2002 |
| 2010/0217273 | A1 | 8/2010 | Someya et al. | WO | WO2005023154 A1 | 3/2005 |
| 2010/0286704 | A1 | 11/2010 | Ichinohe et al. | WO | WO2005070341 A1 | 8/2005 |
| 2011/0082463 | A1 | 4/2011 | Inoue | WO | WO2005084588 A1 | 9/2005 |
| 2011/0098717 | A1 | 4/2011 | Inoue | WO | WO2006070628 A1 | 7/2006 |
| 2011/0270264 | A1 | 11/2011 | Shoji et al. | WO | WO 2006/080191 A1 | 8/2006 |
| 2011/0288557 | A1 | 11/2011 | Kudo et al. | WO | WO 2007/037223 A1 | 4/2007 |
| 2012/0022549 | A1 | 1/2012 | Someya et al. | WO | WO2007037223 A1 | 4/2007 |
| 2012/0071887 | A1 | 3/2012 | Ichinohe et al. | WO | WO2007097221 A1 | 4/2007 |
| | | | | WO | WO2007080869 A1 | 7/2007 |
| FOREIGN PATENT DOCUMENTS | | | | WO | WO2008149794 A1 | 12/2008 |
| EP | | 0363213 | 4/1990 | WO | WO2008149795 A1 | 12/2008 |
| EP | | 0727966 | 9/2003 | WO | WO2009058929 A1 | 7/2009 |
| EP | | 1832247 A1 | 9/2007 | WO | WO2009148091 A1 | 12/2009 |
| EP | | 1338254 | 12/2008 | WO | WO2011126144 A1 | 10/2011 |
| FR | | 2749752 A | 12/1997 | WO | WO2011155636 A1 | 12/2011 |
| JP | | 63-197453 A | 8/1988 | | | |
| JP | | 4-212350 A | 8/1992 | * cited by examiner | | |
| JP | | 5-103808 | 4/1993 | | | |

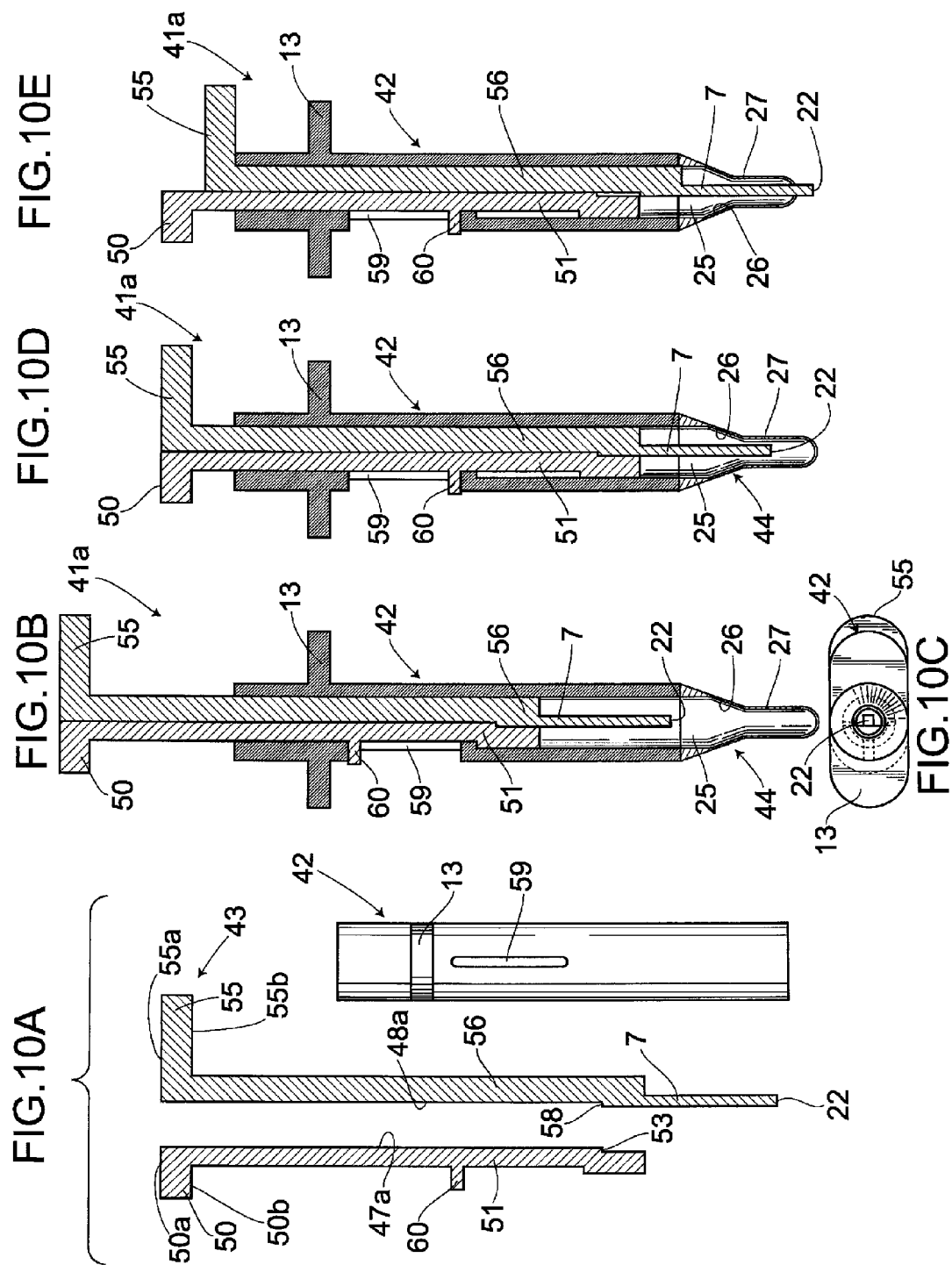

INTRAOCULAR LENS INSERTION DEVICE

TECHNICAL FIELD

The present invention relates to an intraocular lens insertion device for inserting an intraocular lens into an aphakic eye after cataract surgery or into a phakic eye at the time of refractive surgery.

BACKGROUND ART

In recent years, an intraocular lens that can be inserted through a small incision has been available and often used in the clinical setting as phacoemulsification technology prevails, such intraocular lens being provided for alleviating post-surgical astigmatism and invasiveness of surgical procedures, and made of soft materials such as foldable silicon, acrylic resin, hydrogel or the like.

Further, there have also been provided various intraocular lens insertion devices for inserting such foldable intraocular lens through a smaller incision on an eye ball. According to those intraocular lens insertion devices, an intraocular lens folded small is allowed to be pushed out and into an eye through an insertion tube having a cylindrical shape, thus making it possible to insert the intraocular lens into the eye through a significantly smaller incision as compared to a conventional case requiring a pair of tweezers to be used for insertion.

Insertion methods of the intraocular lens insertion devices are broadly divided into a group of screw-type (screw style) and a group of push-type.

A push-type intraocular lens insertion device allows an operator to sensuously press an operation portion with his/her grip strength against resistance such as friction or the like between the intraocular lens and an inner wall of the insertion tube, and allows a pressure thus applied to be transmitted to the intraocular lens so as to push the same forward (e.g., see patent documents 1, 2, 3). According to such push-type intraocular lens insertion device, an insertion operation of the intraocular lens is not only simple, but can be performed with one hand, thereby allowing the operator to use his/her free hand to perform other operations when performing the insertion operation. However, the intraocular lens needs to be moved forward while balancing the friction resistance between the intraocular lens and the inner wall of the insertion tube with the pressure applied to the operation portion, thus making it relatively difficult to control the pressure applied to the operation portion. Further, a nozzle provided on a distal end of the intraocular lens insertion device is the narrowest portion in the insertion tube through which the intraocular lens passes. In this sense, a load generated as the intraocular lens passes through the nozzle becomes large, particularly when releasing an intraocular lens with high power therefrom and when an inner diameter of the nozzle is made small so as to match a smaller incision. Therefore, there is a possibility that the intraocular lens may be abruptly released into the eye, and that eye tissue may thus be damaged.

On the other hand, a screw-type intraocular lens insertion device comprises a plunger and a main body that are screwed together like an external thread and an internal thread. Such screw-type intraocular lens insertion device allows the plunger and a rod for pushing the intraocular lens to move to a lens advancement direction when an operation portion on an end portion of the plunger is twisted (e.g., see patent document 4). According to those screw-type intraocular lens insertion devices, it is easy to control moving amounts of the plunger and the rod. In this sense, the intraocular lens can be prevented to some extent from being abruptly released into the eye, even when the load generated as the intraocular lens passes through the nozzle is large when releasing a thick intraocular lens and the inner diameter of the nozzle is made small. However, since both hands are needed to perform the insertion operation, operation of the screw-type intraocular lens insertion device is relatively more troublesome than that of the push-type intraocular lens insertion device to a certain extent.

Patent document 1: Japanese Unexamined Patent Application Publication (Translation of PCT Application) No. 2000-516487

Patent document 2: Japanese Unexamined Patent Application Publication No. 2003-144480

Patent document 3: Japanese Unexamined Patent Application Publication No. 2004-351196

Patent document 4: Japanese Unexamined Patent Application Publication (Translation of PCT Application) No. Hei 11-506357

DISCLOSURE OF THE INVENTION

Problem to be Solved by the Invention

In order to lower the possibility of abruptly releasing the intraocular lens into the eye when operating the push-type intraocular lens insertion device, there have been employed methods such as providing a slit on a distal end portion of the insertion tube, utilizing a spring to apply to the plunger a force in a direction opposite to a direction to which the lens is pushed, or the like (e.g., Japanese Unexamined Patent Application Publication (Translation of PCT Application) No. Hei 11-510711). However, those methods are not sufficient in terms of preventing the intraocular lens from being abruptly released.

Here, in view of the aforementioned problem, it is an object of the present invention to provide an intraocular lens insertion device capable of more reliably controlling the releasing of an intraocular lens into an eye.

Means for Solving the Problem

The invention according to a first aspect of the present invention is an intraocular lens insertion device for pushing out an intraocular lens by allowing an operation portion thereof to be pushed. This intraocular lens insertion device comprises: a lens contact portion for pushing out the intraocular lens; a transmitting portion for transmitting an external force applied to the operation portion to the lens contact portion; an insertion tube from which the intraocular lens is released to the outside after being pushed by the lens contact portion; and a stop means for temporarily stopping the lens contact portion as the intraocular lens passes through a vicinity of a distal end portion of the insertion tube.

The invention according to a second aspect of the present invention is provided with a plurality of the operation portions, and is thus capable of pushing out the intraocular lens in a step-wise manner.

The invention according to a third aspect of the present invention comprises a main body with the insertion tube fixed to a forward portion thereof, and the operation portion is provided on a backward portion thereof.

The invention according to a fourth aspect of the present invention comprises the main body with the insertion tube fixed to the forward portion thereof, and at least one of the operation portions is provided on the backward portion thereof.

According to the invention described in a fifth aspect through an eighth aspect, the stop means causes the lens contact portion to be temporarily stopped at a location within 10 mm from a distal end of the insertion tube.

According to the invention described in a ninth aspect through a twelfth aspect, the stop means causes the lens contact portion to be temporarily stopped as the intraocular lens passes through a nozzle section provided on the distal end of the insertion tube.

Effects of the Invention

According to the intraocular lens insertion device of the present invention, the stop means causes the lens contact portion to be temporarily stopped as the intraocular lens passes thorough the vicinity of the distal end portion of the insertion tube, thus allowing the lens contact portion to be stopped before the intraocular lens is released even when a large external force against a reaction force of the operation portion is applied. In this way, the intraocular lens is prevented from being abruptly released into the eye. In this sense, the intraocular lens insertion device of the present invention is capable of releasing the intraocular lens with a small external force, thereby making it possible to more reliably control the releasing of the intraocular lens into the eye.

BRIEF DESCRIPTION OF THE DRAWINGS

FIGS. 1A and 1B are cross sectional views showing a structure of an intraocular lens insertion device of a first embodiment of the present invention, in which FIG. 1A shows an overall structure thereof, and FIG. 1B shows a state in which a cartridge is disengaged therefrom.

FIGS. 9A and 9B are cross sectional views showing, in a step-wise manner, usage states of the intraocular lens insertion device of the second embodiment of the present invention, in which FIG. 9A shows a usage state (1), and FIG. 9B shows a usage state (2).

FIGS. 10A, 10B, 10D and 10E are cross sectional views showing a modified embodiment of the intraocular lens insertion device of the second embodiment of the present invention, and FIG. 10C is an end view thereof, in which FIG. 10A is a component formation diagram, FIG. 10B shows a usage state (1), FIG. 10D shows a usage state (2), and FIG. 10E shows a usage state (3).

FIGS. 14A-14C are a series of cross sectional views showing, in a step-wise manner, usage states of the intraocular lens insertion device of the third embodiment of the present invention, in which FIG. 14A shows a first stage of push-out operation, FIG. 14B shows restoration to an operation enabling position, and FIG. 14C shows a second stage of push-out operation.

BEST MODE FOR CARRYING OUT THE INVENTION

Figure 1A:
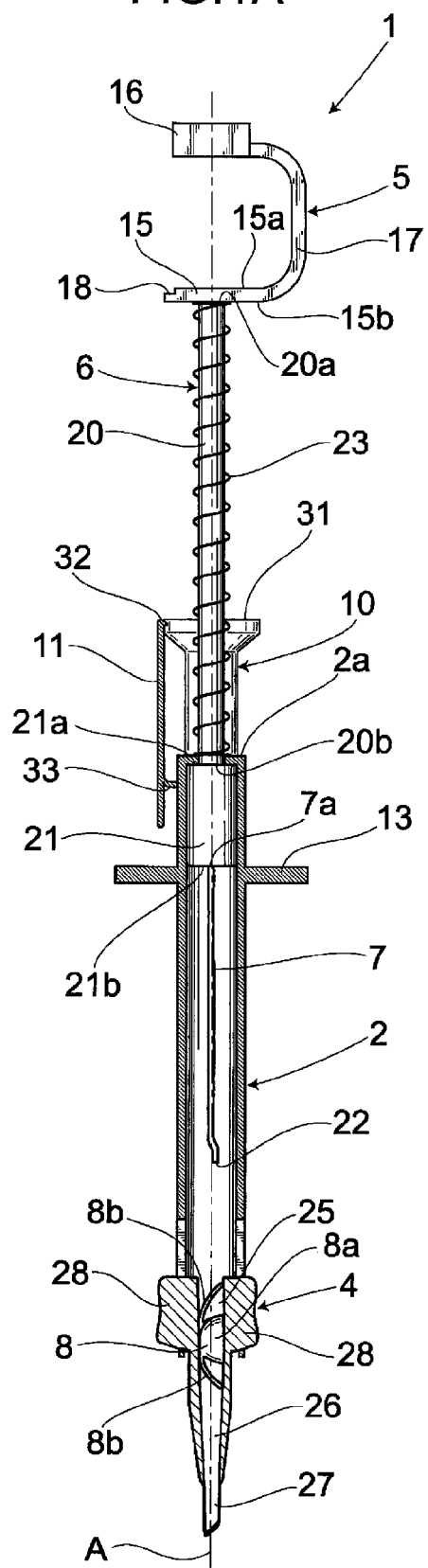

The present invention is capable of lowering the possibility of abruptly releasing an intraocular lens into an eye by allowing a lens contact portion to be temporarily stopped in the vicinity of a distal end portion of an insertion tube, as compared to a case in which the lens contact portion is not stopped.

In a case in which most part of the intraocular lens has been released into the eye from a distal end of the insertion tube after temporarily stopping the lens contact portion, the intraocular lens, without being further pushed, may enter the eye on its own due to an elasticity of the distal end portion of the insertion tube portion. In this case, in order to place the intraocular lens at a predetermined location in the eye, a small force is further applied to an operation portion so as to cause the lens contact portion to move forward, thereby lowering the possibility of abruptly releasing the intraocular lens into the eye.

Further, even when most part of the intraocular lens is remaining in the insertion tube, the momentum of the lens contact portion moving forward can be stopped by temporarily stopping the lens contact portion, thus lowering the possibility of abruptly releasing the intraocular lens into the eye.

A location at which the lens contact portion is temporarily stopped should be determined by various factors including a material of the insertion tube, a shape of a lumen of the insertion tube (such as an asymmetric shape, an oval shape, a rhombic shape, a circular shape or the like), a shape of the distal end portion of the insertion tube (such as a slit, a cut-out or the like), a shape of the intraocular lens including a supporting portion thereof, a material and a flexibility of the intraocular lens, a magnitude of a slide resistance between the intraocular lens and the insertion tube, or the like.

For example, with regard to an intraocular lens insertion device in which a slit is provided on the distal end portion of the insertion tube, the lens contact portion may be temporarily stopped at a location closer to the distal end of the insertion tube as compared to an intraocular lens insertion device in which no slit is provided on the distal end portion of the insertion tube.

Further, the most appropriate setting locations of an intraocular lens with a large flexibility and an intraocular lens with a small flexibility differ from one another.

As a measure of the location at which the lens contact portion is stopped, the lens contact portion may be temporarily stopped at somewhere between a location at which a pushing resistance of the operation portion reaches a maximum value and the distal end of the insertion tube.

As another measure, the location at which the lens contact portion is temporarily stopped may be determined based on a size of an optical portion of the intraocular lens. For example, when a diameter of the optical portion of the intraocular lens is 6 mm, the lens contact portion is temporarily stopped beyond 6 mm from the distal end of the insertion tube inwardly (from a bottom edge of a cut-out when a cut-out is formed on a nozzle section).

As described above, various factors need to be taken into account when determining the location at which the lens contact portion is temporarily stopped. Here, if the lens contact portion is stopped beyond 10 mm from the distal end of the insertion tube inwardly, the operation portion needs to be further pushed with a force almost as large as or lager than a force applied before the lens contact portion is stopped, in order to move the lens contact portion forward. In this sense, significant effect of restricting the intraocular lens from popping out can not be expected.

As a stop means for temporarily stopping the lens contact portion, there can be employed a method for mechanically and forcibly stopping the lens contact portion, a means for forcibly stopping the lens contact portion through an interaction between the intraocular lens insertion device and hands or fingers operating the same, or the like.

The operation portion may comprise a single portion pushed to temporarily stop the lens contact portion and further pushed thereafter. Alternatively, the operation portion may comprise a portion pushed to temporarily stop the lens contact portion and a portion further pushed thereafter. On the other hand, same lens contact portion is preferably used before and after being stopped.

1. First Embodiment (1) Overall Structure

Figure 1B:
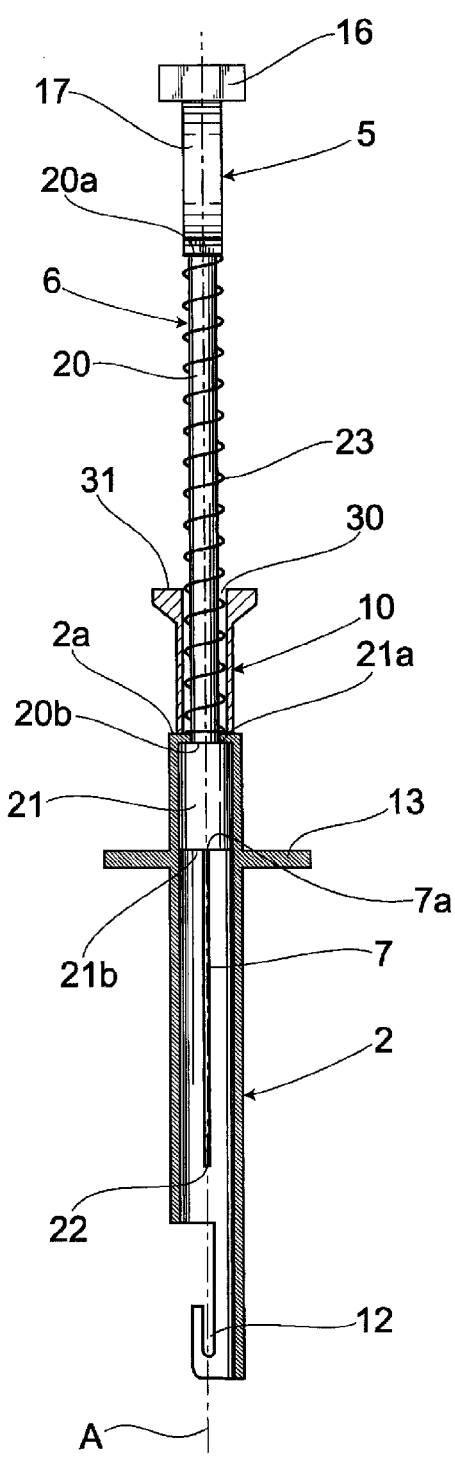

An intraocular lens insertion device 1 shown in FIGS. 1A and 1B comprises a main body 2, a cartridge 4 attached to the main body 2 and an operation portion 5. A plunger 6 serving as a transmitting portion is connected to the operation portion 5. A rod 7 for pushing out an intraocular lens 8 is provided on a distal end of the plunger 6. The operation portion 5 is located away from one end 2a of the main body 2. In this sense, the intraocular lens 8 placed in the cartridge 4 can be pushed out by the rod 7 as a whole as an operator pushes the operation portion 5. Here, a type of disposable insertion tube that allows the operator or an assistant to place the intraocular lens 8 thereinside at the time of operation is generally called a cartridge.

In addition to the aforementioned structure, the intraocular lens insertion device 1 of the present embodiment comprises a stop means described later. Such stop means allows the rod 7 to first push the intraocular lens 8 by a predetermined distance and then be stopped temporarily before the intraocular lens 8 is released from the cartridge 4 toward the outside.

Here, in the following descriptions, a lens advancement direction (push-out direction) is referred to as a "forward direction", while a direction opposite to this direction is referred to as a "backward direction."

The main body 2, the plunger 6 and the rod 7 are preferably formed by an injection-moldable synthetic resin, thus contributing to mass production thereof with low cost and favoring disposability (disposable).

Further, the intraocular lens 8 is made of a soft and foldable material such as silicon resin, acrylic resin, hydrogel or the like, and is unfolded after being released into an eyeball. Here, the intraocular lens 8 shown in FIG. 1A is folded.

The main body 2 is a cylindrical member. A restraint portion 10 serving as a stop means is provided on the one end 2a of the main body 2. Further, the main body 2 has an engagement portion 11 for preventing the operation portion 5 from moving to the backward direction, an attachment groove 12 provided on an other end thereof for attaching the cartridge 4, and a finger rest 13.

The operation portion 5 has a first operation portion 15 and a second operation portion 16. A spacing-keeping portion 17 is connected to proximal ends of both the first operation portion 15 and the second operation portion 16, and is provided for separating the two by a predetermined distance in the lens advancement direction. The operation portion 5 is formed into a tipped "U" shape by bending a substantially rectangular member, and is connected to the plunger 6 through the first operation portion 15 thereof. A surface located on one side of the first operation portion 15 is referred to as a first operation surface 15a. An engagement-receiving portion 18 is provided on a distal end of the first operation portion 15 to which the spacing-keeping portion 17 is not connected.

The plunger 6 is capable of transmitting to the rod 7 an external force applied to the operation portion 5 in a direction of a lens advancement axis A. Further, the plunger 6 has a coil-spring-loaded rod 20 whose one end 20a is connected to an other side surface 15b of the first operation portion 15, and a movable rod 21 connected to an other end 20b of the coil-spring-loaded rod 20. The movable rod 21 is allowed to move either forward or backward inside the main body 2 in the direction of the lens advancement axis A. One end 21a of the movable rod 21 is connected to the other end 20b of the coil-spring-loaded rod 20, while an other end 21b thereof is connected to a proximal end 7a of the rod 7.

The rod 7 is capable of pushing out the intraocular lens 8 by virtue of the external force transmitted by the plunger 6. A lens contact portion 22 is provided on a distal end of the rod 7. Here, a heretofore known shape may be employed as the shape of the lens contact portion 22 provided on the distal end of the rod 7.

A coil spring 23 is disposed on the coil-spring-loaded rod 20 in a manner such that while one end thereof abuts against the one end 2a of the main body 2, the other end thereof abuts against the other side surface 15b of the first operation portion 15. The operation portion 5 is thus biased to the backward direction due to a bias force of the coil spring 23. In this way, the movable rod 21 is caused to be held in a position in which it abuts against an inner wall of the one end 2a of the main body 2. In the present embodiment, the state in which the movable rod 21 abuts against the inner wall of the one end 2a of the main body 2 is referred to as a point of origin, for the sake of convenience in explanation.

The cartridge 4 comprises a lens placement section 25, a transition section 26 and a nozzle section 27, all of which are successively provided along the lens advancement axis A in this order. The intraocular lens 8 placed in the lens placement section 25 is pushed by the rod 7 and is thus caused to move therefrom and then pass through the transition section 26. As a result, the intraocular lens 8 will be folded small and released as it is from the nozzle section 27 toward the outside, such nozzle section 27 having a substantially constant lumen diameter in the direction of the lens advancement axis A.

Further, a wing portion 28 is provided on both sides of the cartridge 4, such wing portion 28 protruding to a direction orthogonal to the lens advancement axis A. The wing portion 28 is so formed that it can be engaged with and fitted to the attachment groove 12 provided on the other end of the main body 2. Here, in starting an operation, a liquid such as a viscoelastic substance or the like allowing the intraocular lens 8 to move smoothly is generally injected into the cartridge 4 before attaching the same to the main body 2.

Figure 2:
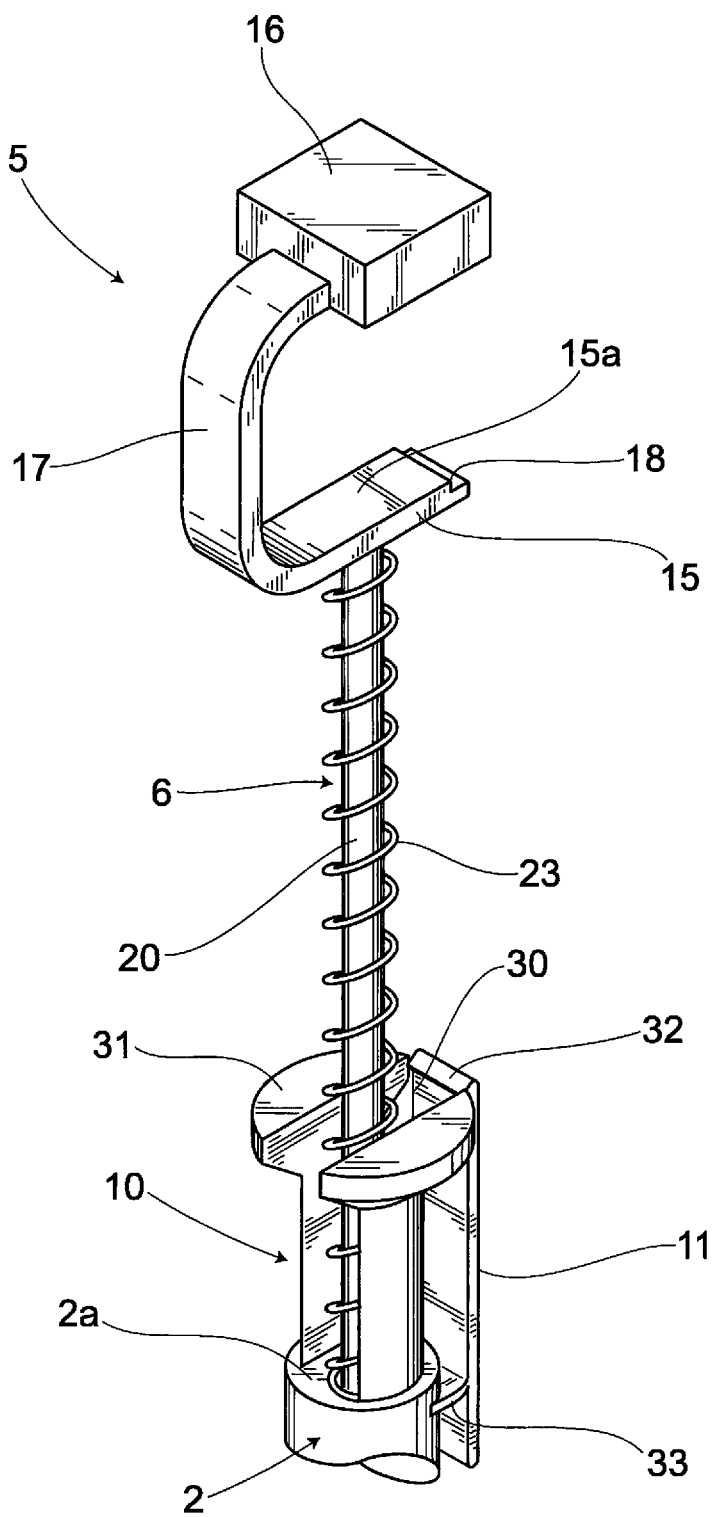
FIG. 2 is a perspective view showing a structure of an operation portion of the intraocular lens insertion device of the first embodiment of the present invention.

The restraint portion 10 serves to restrain the operator's finger pushing the first operation portion 5 at a predetermined position, and the first operation portion 5 can be caused to enter the restraint portion 10. As shown in FIG. 2, one end of the restraint portion 10 is connected to the one end 2a of the main body 2, and the restraint portion 10 has an entrance groove 30 and a restraint surface 31 provided on an other end thereof.

The restraint surface 31 is a surface orthogonal to the lens advancement axis A. The entrance groove 30 substantially cuts through the center of the restraint surface 31, linearly extends in a direction orthogonal to the lens advancement axis A, and is formed through the restraint portion 10 from the one end thereof to the other.

An engagement projection 32 is formed on one end of the engagement portion 11, and is positioned on an outer edge portion where the entrance groove 30 and the restraint surface 31 intersect with one another. The engagement portion 11 is connected to the main body 2 through a connection plate 33 provided on an other end side of the engagement portion 11. Further, the engagement projection 32 is allowed to tilt about the connection plate 33 to a direction orthogonal to the lens advancement axis A.

(2) Operation and Effects

Figure 3:
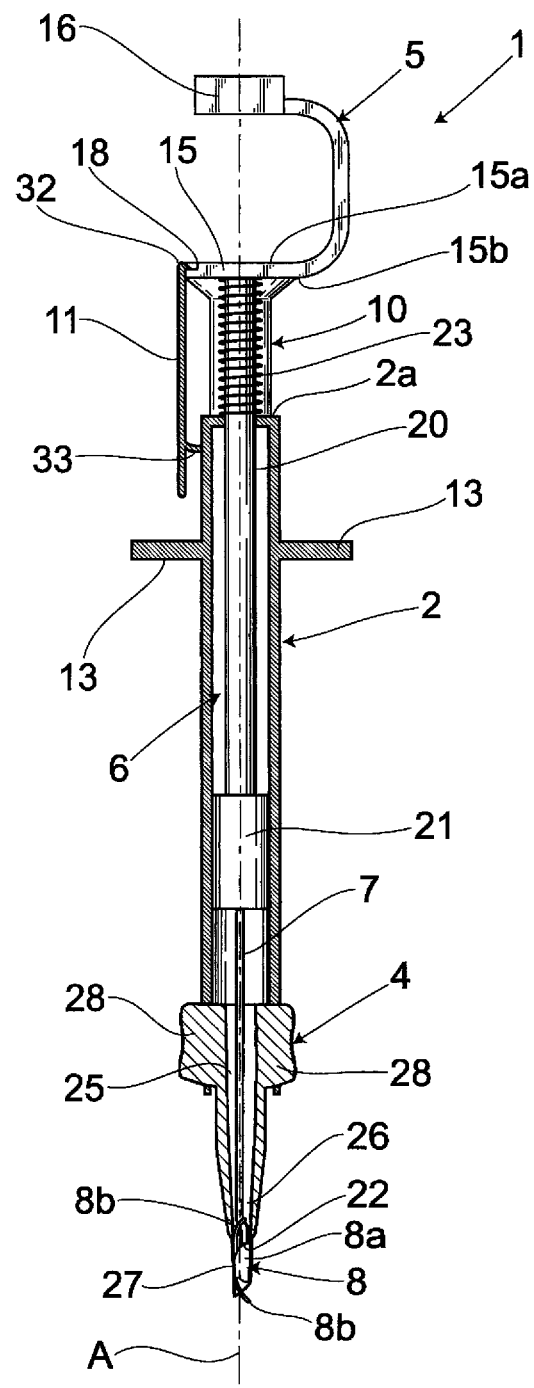
FIG. 3 is a cross sectional view showing a usage state (1) of the intraocular lens insertion device of the first embodiment of the present invention.

According to the aforementioned structure, once the nozzle section 27 has been inserted into the eye, an external force in the forward direction is applied to the operation portion 5 by pushing the first operation surface 15a with fingers from a state of the point of origin of the operation portion 5 (FIG. 1A). As shown in FIG. 3, due to such external force in the forward direction applied to the operation portion 5, the other side surface 15b of the first operation portion 15 is caused to contract the coil spring 23, thereby allowing the plunger 6 and the rod 7 to move to the forward direction.

Figure 4:
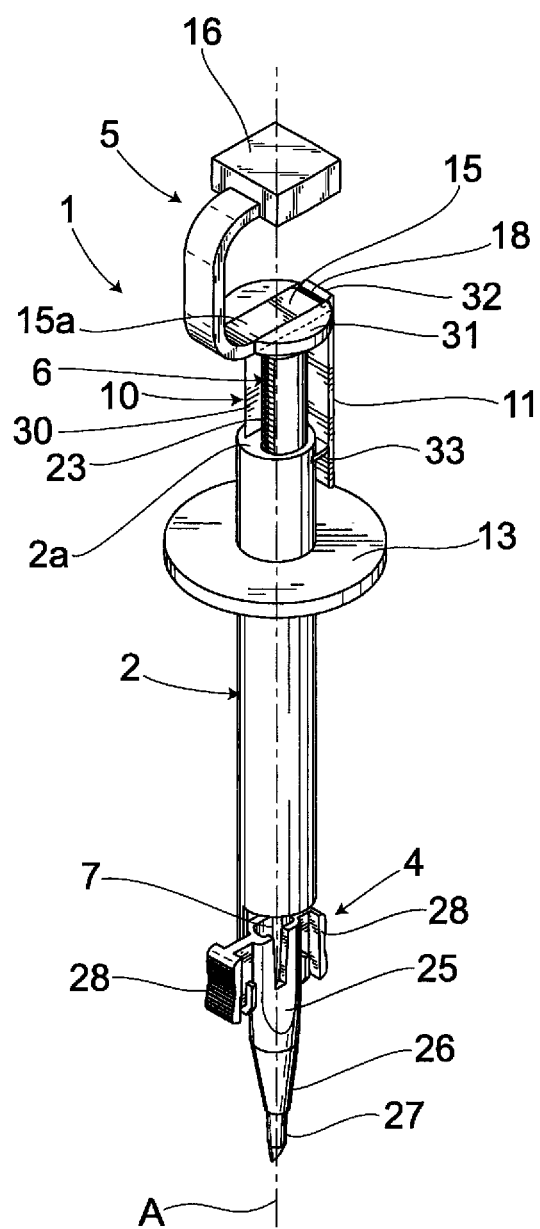
FIG. 4 is a perspective view showing the usage state (1) of the intraocular lens insertion device of the first embodiment of the present invention.

Subsequently, as shown in FIG. 4, the first operation portion 15 arrives at the restraint portion 10, and further enters the entrance groove 30. Here, an operator's finger pushing the first operation surface 15a is caused to abut against the restraint surface 31 as soon as the first operation surface 15a and the restraint surface 31 have been made flush with one another. In this way, the operator is no longer able to push the operation portion 5 to the forward direction any further by pushing the first operation surface 15a, thereby allowing the intraocular lens insertion device 1 to stop the lens contact portion 22 temporarily.

At the same time, the distal end of the first operation portion 15 abuts against the engagement projection 32 of the engagement portion 11. Further, the engagement portion 32 is caused to deform in a direction orthogonal to the lens advancement axis A by further pushing the first operation portion 15. Once the distal end of the first operation portion 15 has been engaged with the engagement portion 32, the engagement portion 11 will elastically return to its original shape. In this way, the engagement-receiving portion 18 of the first operation portion 15 is engaged with the engagement projection 32, thus preventing the operation portion 5 from moving to the backward direction.

By carrying out a first stage of operation as described above, the lens contact portion 22 provided on the distal end of the rod 7 is caused to abut against a circumference of an optical portion 8a of the intraocular lens 8 placed in the cartridge 4, and push such intraocular lens 8 to the forward direction (FIG. 3). According to the present embodiment, the operation portion 5 can no longer be pushed any further to the forward direction by pushing the first operation surface 15a once the first operation surface 15a and the restraint surface 31 have been made flush with one another. In this sense, the intraocular lens insertion device 1 allows the lens contact portion 22 to be stopped temporarily as the intraocular lens 8 passes through the nozzle section 27. In this way, the intraocular lens 8 is allowed to be stopped at a predetermined location after moving from the lens placement section 25 to the transition section 26 and then to the nozzle section 27, successively. Here, the predetermined location refers to a position where the intraocular lens 8 is about to be released from the nozzle section 27 of the cartridge 4. In other words, the intraocular lens 8 at such predetermined location can already be completely released toward the outside once subjected to a moderate amount of force.

Figure 5:
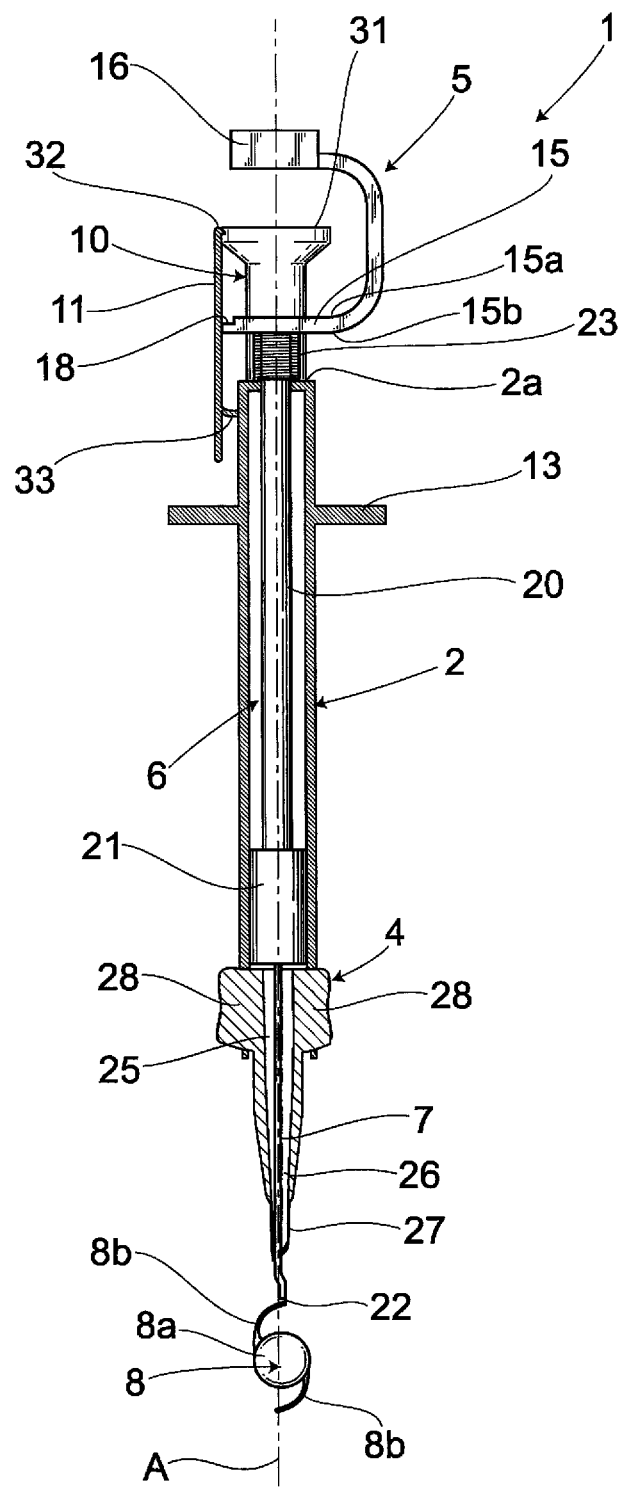
FIG. 5 is a cross sectional view showing a usage state (2) of the intraocular lens insertion device of the first embodiment of the present invention.
Figure 6:
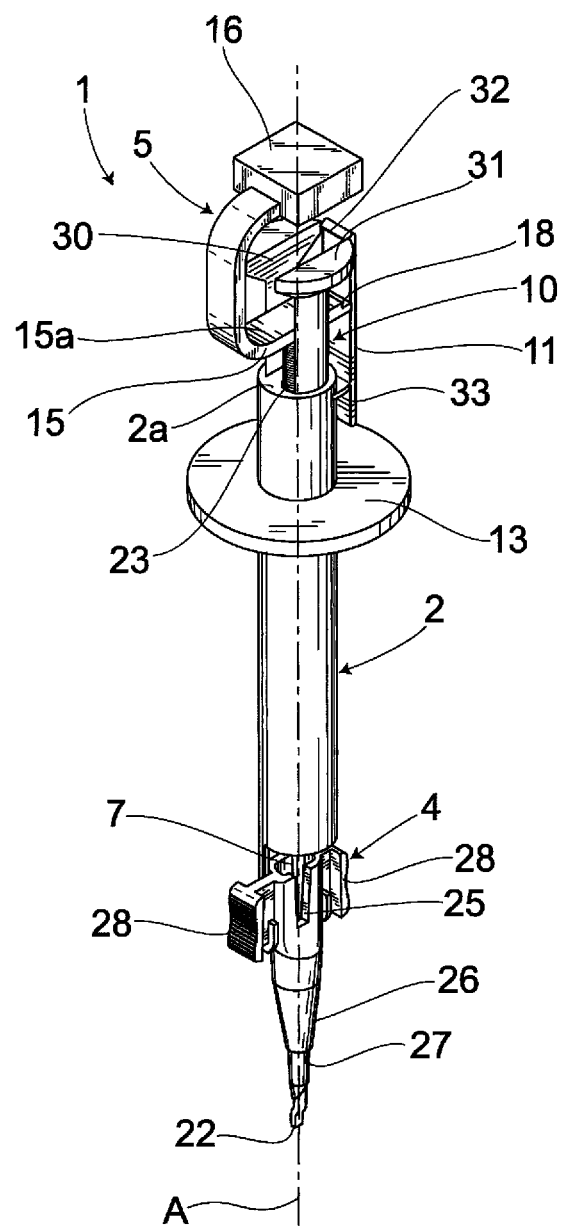
FIG. 6 is a perspective view showing the usage state (2) of the intraocular lens insertion device of the first embodiment of the present invention.

Next, as shown in FIG. 5, the operator applies to the operation portion 5 an external force in the forward direction by pushing the second operation portion 16. The first operation portion 15 is then allowed to move through the entrance groove 30 in the forward direction due to the external force applied to the operation portion 5 in the forward direction (FIG. 6). In this way, the other side surface 15b of the first operation portion 15 is caused to further contract the coil spring 23, thereby allowing the plunger 6 and the rod 7 to move to the forward direction.

As a second stage of operation, since the first operation surface 15a can no longer be pushed, the second operation portion 16 is pushed in order to further push the operation portion 5 into the main body 2, thus allowing the lens contact portion 22 to release the intraocular lens 8 from the nozzle section 27 toward the outside (FIG. 5). After releasing the intraocular lens, the lens contact portion 22 is left protruding from the nozzle section 27, thereby making it possible to also adjust positions of supporting portions 8b and the optical portion 8a of the intraocular lens 8 released in the eye.

The intraocular lens insertion device 1 of the present embodiment allows the lens contact portion 22 for pushing out the intraocular lens 8 to be stopped temporarily before releasing the intraocular lens 8 from the nozzle section 27. Particularly, the lens contact portion 22 can be stopped before releasing the intraocular lens 8, even when a large external force against a reaction force of the operation portion 5 is applied, such reaction force of the operation portion 5 increasing as the intraocular lens 8 passes through the transition section 26 and arrives at the nozzle section 27. In this way, the intraocular lens 8 can be prevented from being abruptly released into the eye. Therefore, the intraocular lens insertion device 1 allows the intraocular lens 8 to be released with a smaller external force at the second stage of operation, thus allowing the intraocular lens 8 to be easily inserted into the eye.

The position at which the lens contact portion 22 is temporarily stopped can be variously determined as described above. For example, the lens contact portion 22 can be temporarily stopped at somewhere in a range between a point when the reaction force of the operation portion 5 has exceeded a maximum value and a point when the intraocular lens 8 is completely released. In this sense, the intraocular lens 8 is allowed to be released with a smaller external force at the second stage of operation. In this way, the intraocular lens 8 can be further reliably prevented from being abruptly released, thus making it easy to insert the intraocular lens 8 into the eye.

Further, according to the intraocular lens insertion device 1 of the present embodiment, the engagement portion 11 prevents the operation portion 5 from moving to the backward direction, once the first operation surface 15a and the restraint surface 31 have been made flush with one another. Therefore, at the second stage of operation, the intraocular lens 8 can be reliably pushed out from a pushed-out position thereof resulting from the first stage of operation, thus allowing the lens contact portion 22 to further reliably capture the intraocular lens 8.

Further, the engagement portion 11 holds the operation portion 5 at a pushed position resulting from the first stage of operation, thereby making it possible to smoothly proceed to the second stage of operation by changing an operation direction of the intraocular lens insertion device 1, and thus allowing the intraocular lens 8 to be easily inserted into the eye.

2. Second Embodiment (1) Overall Structure

According to the aforementioned first embodiment, the lens contact portion is stopped temporarily as the operator's finger pushing the operation portion has come to abut against the stop means. The present embodiment differs from the first embodiment in that a lens contact portion is mechanically stopped temporarily by allowing an operation portion to abut against a stop means. Same reference numbers are used to describe the same parts as those in the aforementioned embodiment, thus omitting the descriptions of such parts for the sake of simplicity.

Figures 7A, 7B:
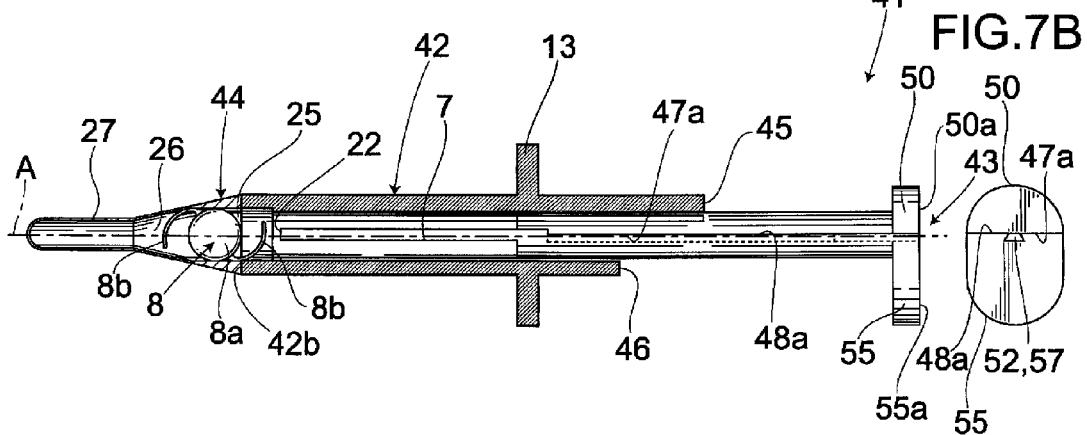
FIG. 7A is a cross sectional view showing an overall structure of an intraocular lens insertion device of a second embodiment of the present invention and FIG. 7B is an end view thereof.

An intraocular lens insertion device 41 shown FIGS. 7A and 7B comprises a main body 42 and an operation portion 43. An insertion tube portion 44 in which an intraocular lens 8 has been placed in advance is attached to the main body 42. In general, the intraocular lens insertion device 41 is a preload type intraocular lens insertion device fixed in a case not shown and packaged as well as shipped with the intraocular lens 8 placed thereinside. Here, in the present embodiment, the insertion tube portion is equivalent to an insertion tube.

The main body 42 is a cylindrical member. A first operation portion receiving surface 45 serving as a stop means is provided on one side across the lens advancement axis A at one end of the main body 42, while a second operation portion receiving surface 46 is provided on an other side across the lens advancement axis A at the one end of the main body 42. The second operation portion receiving surface 46 is located away from the first operation portion receiving surface 45 by a predetermined distance in the forward direction.

The insertion tube portion 44 comprises a lens placement section 25, a transition section 26 and a nozzle section 27, all of which are successively provided along the lens advancement axis A in this order. The insertion tube portion 44 with the intraocular lens 8 placed therein in advance is integrated into the main body 42. Particularly, the insertion tube portion 44 is integrated into the main body 42 by allowing a proximal end thereof to be attached to an attachment portion formed on an other end 42b of the main body 42.

In addition to the aforementioned structure, the operation portion 43 has a first operation portion 50 and a second operation portion 55. The first operation portion 50 and the second operation portion 55 are formed into two halves, and are allowed to move relative to one another in the lens advancement direction A. According to the present embodiment, a plunger serving as a transmitting portion includes a first plunger and a second plunger, as described later.

Figure 8:
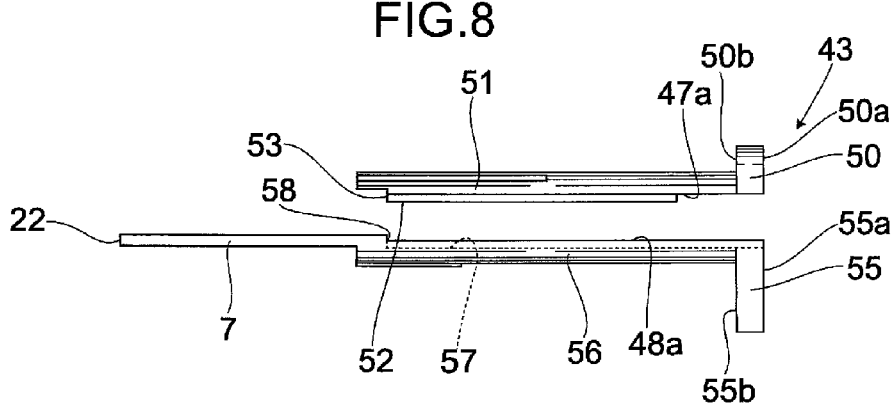
FIG. 8 is a front view showing a structure of an operation portion of the intraocular lens insertion device of the second embodiment of the present invention.

As shown in FIG. 8, the first operation portion 50 comprises a first operation surface 50a formed on a surface of one side thereof, and a first plunger 51 provided on an other side surface 50b. The first plunger 51 has an engagement rib 52 provided on a half surface 47a and having a longitudinal direction identical to the direction of the lens advancement axis A. Further, a push-out surface 53 substantially orthogonal to the lens advancement axis A is formed on a distal end of the first plunger 51.

The second operation portion 55 comprises a second operation surface 55a formed on a surface of one side thereof, and a second plunger 56 provided on an other side surface 55b. Further, a rod 7 is connected to a distal end of the second plunger 56. An engagement groove 57 whose longitudinal direction is identical to the direction of the lens advancement axis A is provided on a half surface 48a of the second operation portion 55. In addition, on the distal end of the second plunger 56, there is provided an abutting surface 58 to be abutted against by the push-out surface 53.

The distal end of the first plunger 51 is inserted toward the second operation surface 55a in the forward direction along the lens advancement axis A, thereby allowing the engagement rib 52 to be engaged with the engagement groove 57 with the half surfaces 47a, 48a facing each other. In this way the first operation portion 50 and the second operation portion 55 are allowed to be integrally combined with one another. Further, the first operation portion 50 and the second operation portion 55 thus combined can slide relative to one another in the forward and backward directions, through the half surfaces 47a, 48a. At that time, the first operation surface 50a and the second operation surface 55a are made flush with one another when the push-out surface 53 has come to abut against the abutting surface 58.

(2) Operation and Effects

Figure 9A:
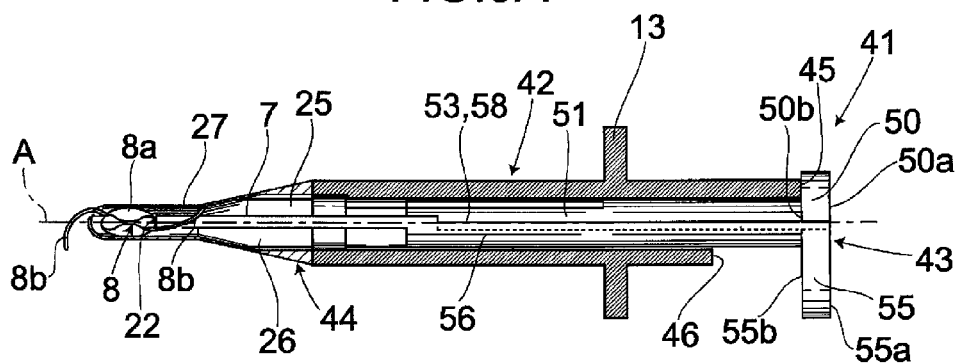

According to the aforementioned structure and as shown in FIG. 9A, the operator pushes the first operation surface 50a in the beginning so as to apply to the first operation portion 50 an external force in the forward direction. Due to such external force applied to the first operation portion 50 in the forward direction, the push-out surface 53 of the first plunger 51 is caused to push out the abutting surface 58 of the second plunger 56, thereby allowing both the first operation portion 50 and the second operation portion 55 to move to the forward direction at the same time.

In this way, the other side surface 50b of the first operation portion 50 is caused to abut against the first operation portion receiving surface 45 of the main body 42. In this sense, the first operation portion 50 can no longer move to the forward direction any further even if the operator continues to push the first operation surface 50a to the forward direction. At that moment, the first operation surface 50a and the second operation surface 55a are still flush with one another.

By carrying out a first stage of operation as described above, a lens contact portion 22 provided on a distal end of the rod 7 is caused to abut against a circumference of an optical portion 8a of the intraocular lens 8 placed in the insertion tube portion 44, and push such intraocular lens 8 to the forward direction. According to the present embodiment, the intraocular lens insertion device 41 allows the lens contact portion 22 to be temporarily stopped as the intraocular lens 8 passes through the nozzle section 27. In this way, the intraocular lens 8 is allowed to move from the lens placement section 25 to the transition section 26 and then to the nozzle section 27, successively, and be stopped at a predetermined location.

Figure 9B:
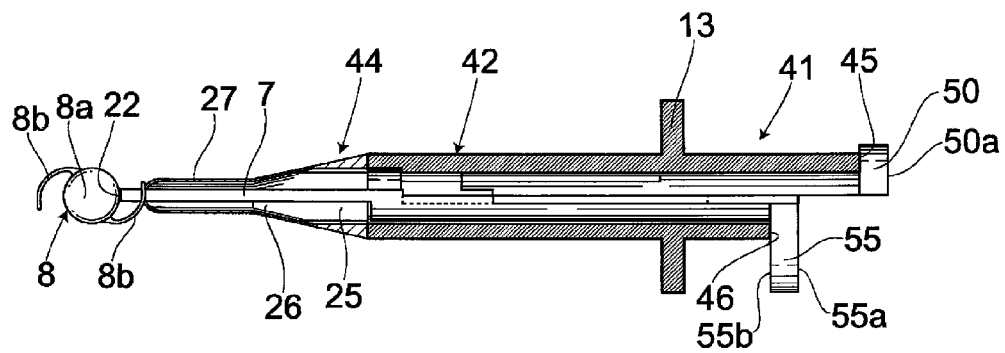

Next, as shown in FIG. 9B, the operator pushes the second operation surface 55a so as to apply to the second operation portion 55 an external force in the forward direction. Since the second operation portion receiving surface 46 is located away from the first operation portion receiving surface 45 by the predetermined distance in the forward direction, the second operation portion 55 is allowed to move to the forward direction alone and independently from the first operation portion 50 due to the external force applied to the second operation portion 55 in the forward direction.

In this way, by carrying out a second stage of operation in which the second operation portion 55 is further pushed into the main body 42 while the first operation portion 50 can no longer be pushed any further, the intraocular lens 8 is released from the nozzle section 27 toward the outside by means of the lens contact portion 22. After releasing the intraocular lens, the lens contact portion 22 is left protruding from the nozzle section 27, thereby making it possible to also adjust positions of supporting portions 8b and the optical portion 8a of the intraocular lens 8 released in the eye.

The intraocular lens insertion device 41 of the present embodiment allows the lens contact portion 22 for pushing out the intraocular lens 8 to be stopped temporarily before releasing the intraocular lens 8 from the nozzle section 27, thereby achieving the same effect as that of the first embodiment.

Further, the second operation surface 55a and the first operation surface 50a are flush with one another when starting the second stage of operation, thereby making it possible to start the second stage of operation by only moving a finger pressing the first operation surface 50a to the second operation surface 55a.

Furthermore, the intraocular lens insertion device 41 of the present embodiment does not require loading the intraocular lens 8 into the cartridge 4 at the time of operation or attaching such cartridge 4 to the main body 42, thus making it possible to reduce errors in handling.

Furthermore, the intraocular lens insertion device 41 of the present embodiment is provided as a disposable system comprising the main body 42, the intraocular lens 8 and the insertion tube portion 44, all of which are designed for one-time use, thereby significantly reducing the risk of infection.

Furthermore, the intraocular lens insertion device 41 of the present embodiment is so packaged that it is fixed in a case not shown, thus preventing the operation portion 43 from being unintentionally pushed to the forward direction at the time of storing and shipping.

(3) Modified Embodiment

An intraocular lens insertion device 41a shown in FIGS. 10-10E differs from the second embodiment in that a stop means thereof is a slide hole 59 provided on a main body 42, such slide hole 59 being formed into a shape of oval parallel with the lens advancement axis A. Further, there is provided on a first plunger 51 a stop pin 60 protruding toward a direction orthogonal to the lens advancement axis A. The first plunger 51 is inserted into the main body 42 with the stop pin 60 thereof being inserted into the slide hole 59, and is allowed to perform piston action as the stop pin 60 moves to the forward and back directions within a range of the slide hole 59.

According to the intraocular lens insertion device 41a of the present modified embodiment, a lens contact portion 22 can be stopped before an intraocular lens 8 is released from a nozzle section 27, by allowing the stop pin 60 to abut against a forward end 59a of the slide hole 59, thus achieving the same effect as that of the first embodiment.

3. Third Embodiment (1) Overall Structure

An intraocular lens insertion device of the present embodiment differs from the aforementioned first embodiment in that it comprises a knock mechanism. Here, same reference numbers are used to describe the same parts as those in the aforementioned embodiments, thus omitting the descriptions of such parts for the sake of simplicity.

Figure 11:
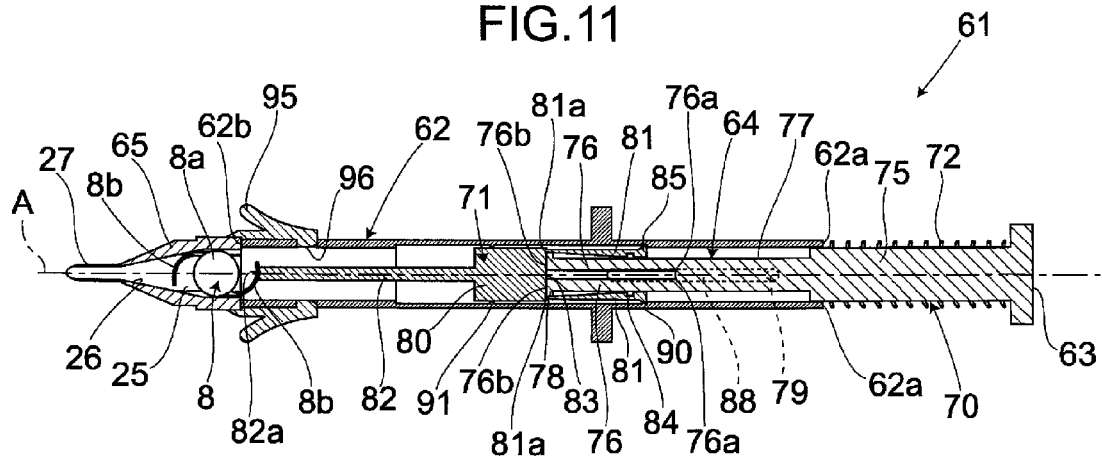
FIG. 11 is a cross sectional view showing an overall structure of an intraocular lens insertion device of a third embodiment of the present invention.

An intraocular lens insertion device 61 shown in FIG. 11 comprises a main body 62, an operation portion 63, a knock mechanism 64 allowing the operation portion 63 to move to the forward and backward directions with respect to the main body 62 and a cartridge 65 attached to an other end 62b of the main body 62. Overall, the knock mechanism 64 repeatedly causes the operation portion 63 to move to the forward and backward directions, thereby allowing an intraocular lens 8 placed in the cartridge 65 to be pushed out in a step-wise manner.

The knock mechanism 64 is capable of pushing the intraocular lens 8 by a predetermined distance as the operation portion 63 is pushed to the forward direction, and allowing the operation portion 63 thus pushed to the forward direction to automatically move to the backward direction. The knock mechanism 64 has a plunger 70 integrally formed on the operation portion 63 and serving as a transmitting portion, a rod 71, a coil spring 72 serving as a restoring member for biasing the plunger 70 to the backward direction, i.e., a moving-back direction, and later described engagement sections provided on an inner surface of the main body 62.

Here, the main body 62, the plunger 70 and the rod 71 are preferably formed by an injection-moldable synthetic resin, thus contributing to mass production thereof with low cost and favoring disposability (disposable).

The plunger 70 restricts a range of movement of the operation portion 63 to a predetermined range, and functions as a pushing force transmitting portion for transmitting an external force applied to the operation portion 63 by the operator to a lens contact portion 82a provided on a distal end of a push-out axis 82 of the rod 71. The plunger 70 has an axis body 75 whose one end is provided with the operation portion 63, and a pair of push-out members 76, 76 formed on an other end of the axis body 75. The operation portion 63 is integrated with the axis body 75, and is formed into a shape of a disk by centrifugally expanding the one end of the axis body 75 in diameter.

The axis body 75 is equipped with the coil spring 72, and is so formed that it can be movably inserted into the main body 62. The pair of the push-out members 76, 76, is provided on the other end of the axis body 75 through a narrow joining section 77. Further, there is provided on the conjunction portion 77 a stop pin 79 protruding toward a direction orthogonal to the lens advancement axis A.

The pair of the push-out members 76, 76 is provided across the lens advancement axis A, and is formed into a branched shape on a distal end of the joining section 77, substantially parallel with the lens advancement axis A. This pair of the push-out members 76, 76 is allowed to elastically deform about proximal ends 76a, 76a connected to the joining section 77 and toward a direction orthogonal to the lens advancement axis A. Further, convex portions 78 protruding outwardly are formed on distal ends 76b, 76b of the push-out members 76, respectively.

The rod 71 is not integrated with the plunger 70, but provided independently therefrom. The rod 71 is capable of pushing out the intraocular lens 8 due to the external force transmitted thereto from the plunger 70. The rod 71 has a sliding body 80, a pair of engagement members 81, 81 provided on one end of the sliding body 80, and the push-out axis 82 provided on an other end of the sliding body 80.

The sliding body 80 is a cylindrical member whose outer diameter is so large that the sliding body 80 is allowed to be movably inserted into the main body 62. The sliding body 80 is also capable of holding the push-out axis 82 on the lens advancement axis A. Further, the sliding body 80 has a substantially flat abutting surface 83 provided on the one end thereof, such abutting surface 83 being orthogonal to the lens advancement axis A.

The pair of the engagement members 81, 81 extends from a vicinity of an outer edge of the sliding body 80, and is formed across and substantially parallel with the lens advancement axis A. The engagement members 81, 81 are so formed that they become thinner from distal ends thereof toward proximal ends 81a connected to the sliding body 80. The engagement members 81, 81 are also allowed to elastically deform about such proximal ends 81a and toward a direction orthogonal to the lens advancement axis A. Further, on inner sides of the distal ends of the engagement members 81, 81, there are respectively provided concave portions 84 with which the aforementioned convex portions 78 are to be engaged. And, on outer sides of the distal ends of the engagement members 81, 81, there are respectively formed projections 85.

Here, on both sides of the cartridge 65, there is provided a wing portion 95 capable of elastically deforming toward a direction orthogonal to the lens advancement axis A. An engagement projection 96 is respectively provided on an inner side of a rear end of each wing portion 95. The cartridge 65 is so formed that the rear end of the wing portion 95 is caused to elastically deform toward the outside once an external force has been applied to a distal end of the wing portion 95 from the outside to the inside.

Figure 12:
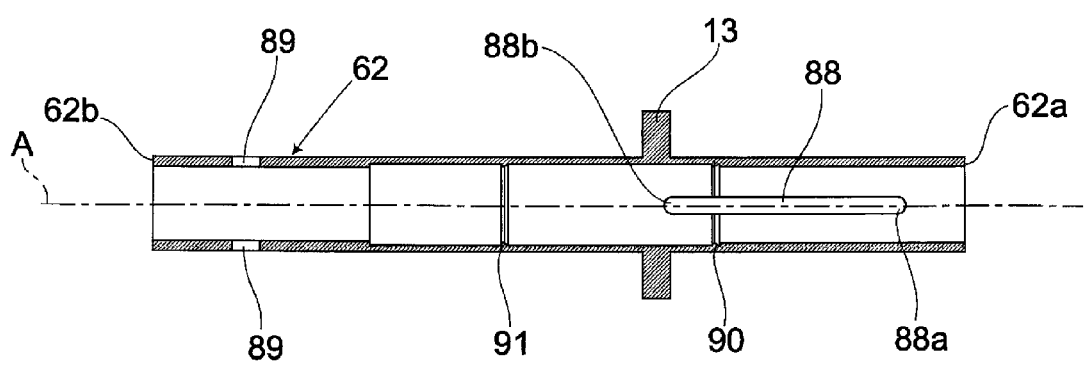
FIG. 12 is a cross sectional view showing a main body of the intraocular lens insertion device of the third embodiment of the present invention.

As shown in FIG. 12, the main body 62 is a cylindrical member and has an oval slide hole 88 provided on a surface located on a side of one end 62a, such slide hole 88 serving as a stop means and being parallel with the lens advancement axis A. Further, on a surface located on a side of an other end 62b of the main body 62, there are respectively provided, across the lens advancement axis A, rectangular receiving holes 89, 89 with which the engagement projections 96 of the cartridge 65 are to be engaged.

In addition, on an inner circumferential surface of the main body 62, there are provided a fixation concave portion 90 for fixing the rod 71, and a restriction convex portion 91 for restricting the rod 71 from moving back to the backward direction, both of which serve as the aforementioned engagement sections.

Figure 13:
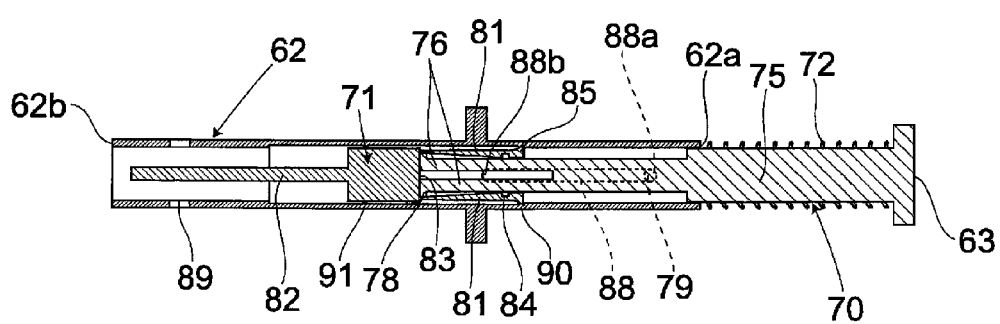
FIG. 13 is a cross sectional view showing a state in which a knock mechanism is mounted on the main body of the intraocular lens insertion device of the third embodiment of the present invention.

Next, the plunger 70 equipped with the coil spring 72 is inserted toward the one end 62a of the main body 62, beginning with the push-out members 76. At that time, the push-out members 76 are caused to pass between the engagement members 81 of the rod 71, and the plunger 70 is kept being inserted into the main body 62 until the distal ends 76b of the push-out members 76 have come to abut against the abutting surface 83 (FIG. 13).

Further, the stop pin 79 provided on the joining section 77 of the plunger 70 is movably inserted into the slide hole 88 of the main body 62. In this way, the plunger 70 is allowed to move to the forward and backward directions within a range defined by the stop pin 79 abutting against one end 88a and an other end 88b of the slide hole 88. In this sense, the operation portion 63 is allowed to move forward and backward in parallel with the lens advancement axis A.

In the following description, a location of the operation portion 63 (plunger 70) when the stop pin 79 abuts against the one end 88a of the slide hole 88 is referred to as a point of origin. And, a location of the operation portion 63 (plunger 70) when the stop pin 79 abuts against the other end 88b of the slide hole 88 is referred to as a push-out point.

Further, the coil spring 72 is disposed between the one end 62a of the main body 62 and the operation portion 63, and serves to bias the operation portion 63 to the backward direction. When the operation portion 63 has been moved to the forward direction, the coil spring 72 is capable of restoring the same to an operation enabling position.

Here, the operation enabling position refers to a position of the operation portion 63 when it can be further pushed to the forward direction, namely, a state in which the stop pin 79 is located away from the other end 88b of the slide hole 88 toward the one end 88a thereof in the present embodiment. In this sense, the operation enabling position is not limited to a location of the operation portion 63 when the stop pin 79 abuts against the one end 88a of the slide hole 88.

The cartridge 65 with the intraocular lens 8 placed therein is attached to the main body 62 having the knock mechanism 64. The rear end of the wing portion 95 is caused to elastically deform toward the outside once the external force has been applied to the distal end of the wing portion 95 from the outside to the inside, thereby allowing the cartridge 65 to be inserted into the other end 62b of the main body 62. At that time, once the external force applied to the distal end of the wing portion 95 has been removed, the wing portion 95 will be elastically restored, thereby causing the engagement projections 96 to be engaged with the receiving holes 89, and thus allowing the cartridge 65 to be attached and fixed to the main body 62 (FIG. 11).

In this way, the intraocular lens insertion device 61 is obtained, such intraocular lens insertion device 61 allowing the intraocular lens 8 to be pushed out by means of the knock mechanism 64, and released from the cartridge 65 when it is folded small.

(2) Operation and Effects

Figure 14A:
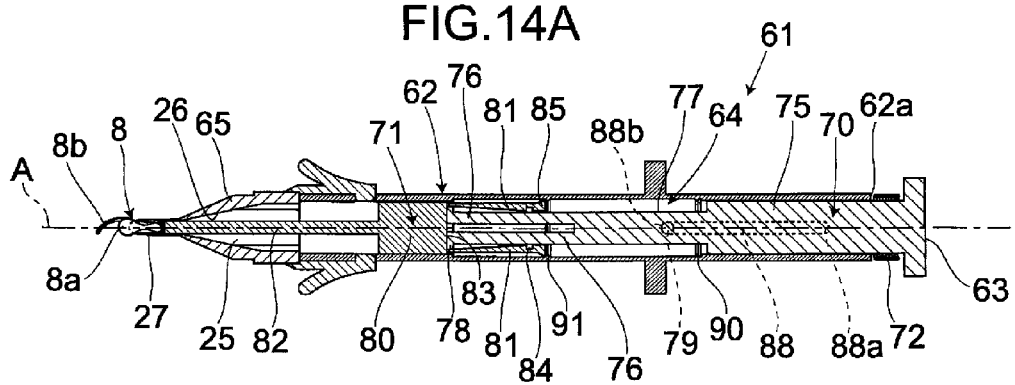

According to the aforementioned structure, the projections 85 will be disengaged from the fixation concave portion 90 of the main body 62 due to the external force applied to the operation portion 63 in the forward direction at the time of pushing the operation portion 63 into the main body 62 from the point of origin (FIG. 11). At that time, as shown in FIG. 14A, the plunger 70 and the rod 71 are caused to move to the forward direction with contraction of the coil spring 72.

Here, the stop pin 79 provided on the plunger 70 is allowed to move from the one end 88a toward the other end 88b within the slide hole 88 provided on the main body 62, thereby allowing the plunger 70 and the rod 71 to freely perform piston action by a distance between the one end 88a and the other end 88b of the slide hole 88. In this way, the plunger 70 and the operation portion 63 will be mechanically stopped at the push-out point once the stop pin 79 of the plunger 70 has arrived at the other end 88b of the slide hole 88 of the main body 62. At that time, the plunger 70 and the operation portion 63 can no longer move to the forward direction.

Also, at that time, the engagement members 81, 81 are caused to elastically deform inwardly with respect to the lens advancement axis A as the rod 71 moves to the forward direction, thereby allowing the projections 85 to move across the restriction convex portion 91 of the main body 62.

Figure 14B:
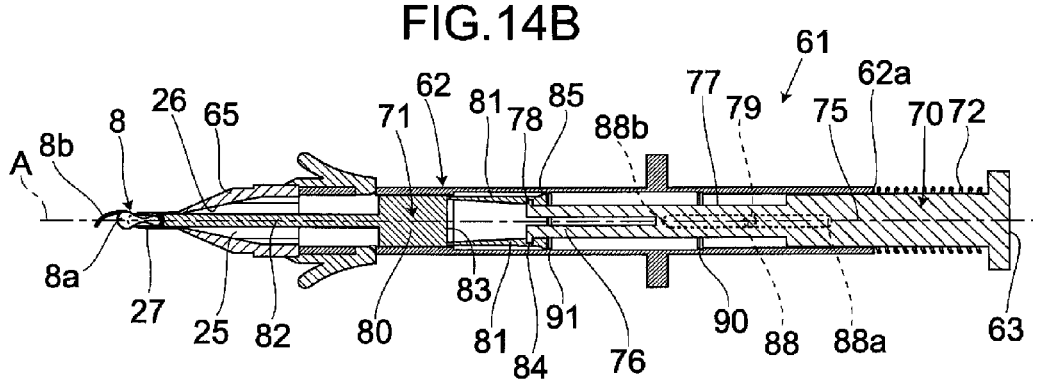

Next, as shown in FIG. 14B, once the external force applied to the operation portion 63 has been removed, the plunger 70 will move to the backward direction due to a bias force of the coil spring 72. Here, the stop pin 79 provided on the plunger 70 is allowed to move from the other end 88b (push-out point) toward the one end 88a within the slide hole 88.

In this sense, the push-out members 76 are caused to move in between the engagement members 81, 81 to the backward direction as the operation portion 63 moves from the push-out point toward the one end 88a. At that time, the projections 85 of the engagement members 81, 81 are engaged with the restriction convex portion 91 of the main body 62, thus stopping the rod 71 and restricting the same from moving to the backward direction. Also, at that time, the convex portions 78 of the push-out members 76 are caused to be engaged with the concave portions 84 of the engagement members 81, 81. In this way, the plunger 70 and the operation portion 63 are restored to the operation enabling position.

By carrying out a first stage of operation as described above, the lens contact portion 82a on the distal end of the push-out axis 82 is caused to abut against the circumference of the optical portion 8a of the intraocular lens 8 placed in the cartridge 65, thereby allowing the rod 71 to push the intraocular lens 8 to the forward direction. According to the present embodiment, the intraocular lens insertion device 61 allows the lens contact portion 82a to be stopped temporarily as the intraocular lens 8 passes through the nozzle section 27. In this sense, the intraocular lens 8 moves from the lens placement section 25 to the transition section 26 and then to the nozzle section 27, and then, stops at a predetermined location.

Figure 14C:
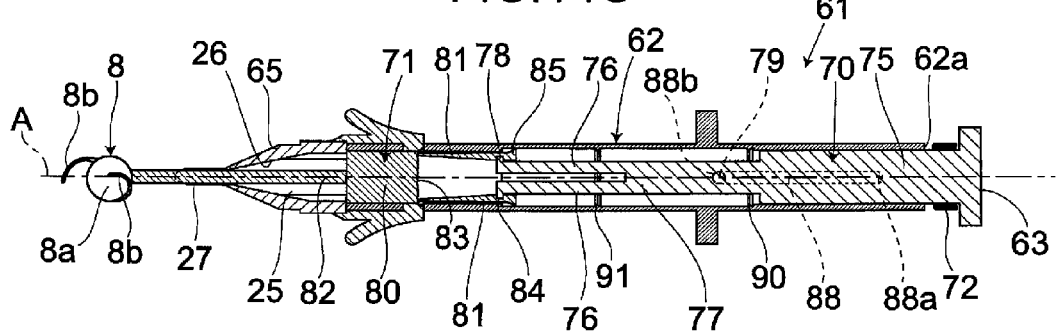

Next, as shown in FIG. 14C, since the convex portions 78 of the push-out members 76 are engaged with the concave portions 84 of the engagement members 81, 81, both the plunger 70 and the rod 71 are allowed to move to the forward direction when further pushing the operation portion 63 restored to the operation enabling position into the main body 62.

Here, the stop pin 79 of the plunger 70 in the operation enabling position is also allowed to move therefrom toward the other end 88b within the slide hole 88 provided on the main body 62. In this way, the plunger 70 will be mechanically stopped at the push-out point once the stop pin 79 has arrived at the other end 88b of the slide hole 88.

In this way, the push-out axis 82 is caused to release the intraocular lens 8 from the nozzle section 27 toward the outside by carrying out a second stage of operation in which the operation portion 63 restored to the operation enabling position is again pushed into the main body 62. After releasing the intraocular lens, the lens contact portion 82a of the push-out axis 82 is left protruding from the nozzle section 27, thereby making it possible to also adjust supporting portions 8b, 8b of the intraocular lens 8 released in the eye and the position of the intraocular lens 8.

The intraocular lens insertion device 61 of the present embodiment comprises the knock mechanism 64 for automatically restoring the operation portion 63 to the operation enabling position, such operation portion 63 being pushed to push out the intraocular lens 8. In this sense, the operator is not required to push out the intraocular lens 8 from a placement location thereof and then release the same with only one long stroke of pushing, thereby making it easy to control an operation pressure applied to the operation portion 63. Further, the length of a stroke for each push-out action can be short even when operating with one hand, thus making one-handed operation easy.

Further, according to the present embodiment, the intraocular lens insertion device 61 allows the intraocular lens 8 to be released to the outside by allowing the operation portion 63 to be pushed to the forward direction twice. In this way, a moving amount of the operation portion 63 can be reduced as compared to a conventional case in which the intraocular lens 8 is released to the outside with one-time action, thereby making it easy for the operator to adjust a moving amount of the intraocular lens 8.

Furthermore, by carrying out the first stage of operation, the intraocular lens insertion device 61 allows the intraocular lens 8 to be mechanically stopped at a location where the intraocular lens 8 is about to be released from the nozzle section 27 of the cartridge 65, thus requiring no expertise to prevent the intraocular lens 8 from being abruptly released into the eye. Particularly, the intraocular lens 8 is already folded small when passing through the nozzle section 27, thus requiring the operation portion 63 to be strongly pushed to the forward direction in order to push out the intraocular lens 8. However, by carrying out the first stage of operation, the lens contact portion 82a is allowed to be mechanically stopped at the location where the intraocular lens 8 is about to be released from the nozzle section 27, thereby preventing the intraocular lens 8 from being abruptly released even when a force pushing the operation portion 63 is strong, and thus releasing the intraocular lens 8 more safely.

Furthermore, by carrying out the second stage of operation requiring the operation portion 63 to be pushed strongly, the intraocular lens insertion device 61 allows the operation portion 63 to be automatically restored to the operation enabling position, thereby allowing the operator to operate the operation portion 63 at the same operation enabling position as that of the first stage of operation, thus making it easier to insert the intraocular lens 8 into the eye.

Furthermore, according to the present embodiment, the operation portion 63 is located behind the main body 62, thereby making an insertion operation of the intraocular lens 8 easier and one-handed operation possible so that the operator may use his/her free hand to perform other operations even at the time of performing the insertion operation.

Furthermore, according to the present embodiment, the coil spring 72 serves to bias the operation portion 63 to the backward direction, thereby allowing the operation portion 63 to be more reliably restored to the operation enabling position.

According to the aforementioned embodiment, the knock mechanism 64 has the plunger 70 integrally formed on the operation portion 63, the rod 71, the coil spring 72 serving as a biasing member for biasing the plunger 70 to the backward direction, i.e., a moving-back direction, and the engagement sections provided on the inner surface of the main body 62. However, the present invention is not limited to such configuration. As a matter of fact, a knock mechanism for use in a so called mechanical pencil can be employed as the knock system as long as the operation portion can be automatically restored to the operation enabling position. Further, other than the coil spring, a leaf spring, an elastic rubber or the like can be employed as the restoring member.

Further, according to the aforementioned embodiment, the intraocular lens is released to the outside by pushing the operation portion into the main body twice. However, the present invention is not limited to such configuration. As a matter of fact, the operation portion can be pushed into the main body three, four or even more times as long as the operation portion can be automatically restored to the operation enabling position.

(3) Modified Embodiment

Figure 15:
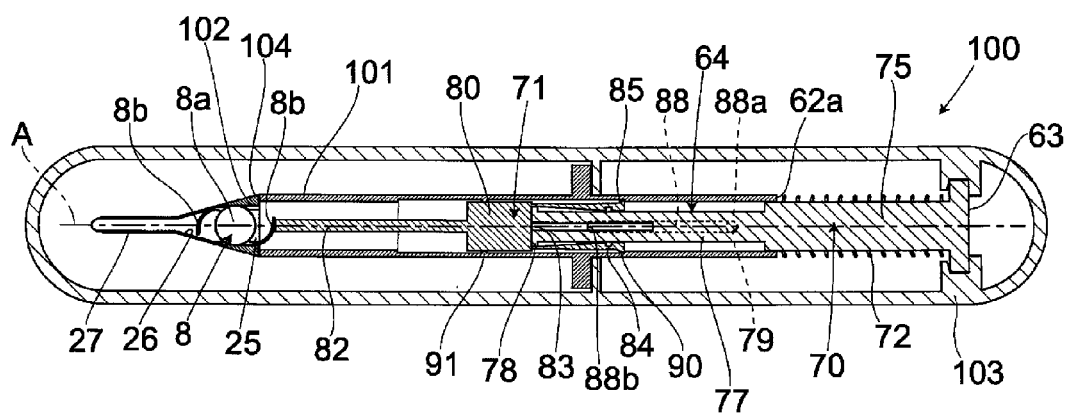
FIG. 15 is a cross sectional view showing a modified embodiment of the intraocular lens insertion device of the third embodiment of the present invention.

An intraocular lens insertion device 100 shown in FIG. 15 comprises a main body 101, an operation portion 63 and a knock system 64. An insertion tube portion 102 in which an intraocular lens 8 is placed in advance is attached to the main body 101. The intraocular lens insertion device 100 is a pre-load type intraocular lens insertion device fixed in a case 103 and packaged as well as shipped with the intraocular lens 8 placed thereinside. Instead of a rectangular receiving hole with which a cartridge is to be engaged, an attachment portion 104 for attaching the insertion tube portion 102 is provided on a distal end of the main body 101.

According to the aforementioned structure, the intraocular lens 8 is allowed to be released to the outside through two stages of operation just like the present embodiment. Further, the operation portion 63 is allowed to be automatically restored to an operation enabling position by means of the knock mechanism 64 at the time of operation.

The intraocular lens insertion device 100 of the present embodiment comprises the knock system 64 for automatically restoring the operation portion 63 to the operation enabling position, such operation portion 63 being pushed to push out the intraocular lens 8. In this sense, the same effect as that of the first embodiment can be achieved with the present embodiment.

Further, the intraocular lens insertion device 100 of the present embodiment is so packaged that it is actually fixed in the case 103, thus preventing the plunger 70 from being unintentionally pushed to the forward direction at the time of storing and shipping.

4. Other Embodiments

According to the aforementioned embodiments, the lens contact portion is left protruding from the nozzle section after releasing the intraocular lens to the outside. However, the present invention is not limited to such configuration. As a matter of fact, the lens contact portion may be configured to stay in the nozzle section, and the intraocular lens can be slowly released into the eye due to a shape recoverability thereof resulting from its elastic nature, even after the lens contact portion has stopped moving to the forward direction.

Furthermore, according to the aforementioned embodiments, the operation portion is allowed to move forward and backward in parallel with the lens advancement axis. However, the present invention is not limited to such configuration. As a matter of fact, the operation portion may be configured to move forward and backward in a direction orthogonal to the lens advancement axis. In this case, the operation portion is, for example, provided on a side surface of the main body, and the push-out point is located on an inner side direction (forward direction) of the main body, while the point of origin is located on an outer side direction (backward direction) thereof.

Furthermore, according to the aforementioned embodiments, the plunger serves as a transmitting portion. However, the present invention is not limited to such configuration. As a matter of fact, a link mechanism, a cam mechanism or the like can be employed as a transmitting portion by which the external force applied to the operation portion is transmitted to the lens contact portion.

Furthermore, according to the aforementioned embodiments, the insertion tube portion comprises the lens placement section. However, the present invention is not limited to such configuration. As a matter of fact, the insertion tube portion needs to comprise only the transition section and the nozzle section, and in such case, the lens placement section may be provided in the main body.

Here, the present invention can be applied to intraocular lens insertion devices of various embodiments such as those disclosed in Japanese Unexamined Patent Application Publication (Translation of PCT Application) No. 2008-521535, Japanese Unexamined Patent Application Publication (Translation of PCT Application) No. 2001-502563, Germany Patent No. 4110278, Japanese Unexamined Patent Application Publication No. Hei 4-212350, and Japanese Unexamined Patent Application Publication No. Sho 63-197453.

The invention claimed is:

1. An intraocular lens insertion device, comprising:
a main body with a lens advancement axis extending therethough;
an elongate member, including a lens contact portion, that is movable in a forward direction along the lens advancement axis from an initial pre-use position to a fully extended position;
a first operating portion that is configured to be pushed by a finger in the forward direction and is connected to the elongate member such that forward movement of the first operating portion results in forward movement of the elongate member;
a second operating portion, located rearwardly of the first operating portion, that is configured to be pushed by a finger in the forward direction and is connected to the elongate member such that forward movement of the second operating portion results in forward movement of the elongate member; and
a restraint associated with the main body and configured to allow the first operating portion to pass from a position rearward of the restraint to a position forward of the restraint and to prevent a finger from pushing the first operating portion to the position forward of the restraint;
wherein the elongate member will be located between the pre-use position and the fully extended position when the restraint prevents a finger from pushing the first operating portion to the position forward of the restraint; and
wherein the restraint will not prevent the second operating portion from moving forwardly to a position that results in the elongate member being in the fully extended position.

2. An intraocular lens insertion device as claimed in claim 1, wherein
the elongate member include a rod and a plunger;
the rod includes the lens contact portion; and
the first and second operating portions are connected to the plunger.

3. An intraocular lens insertion device as claimed in claim 1, further comprises:
a bias element, associated with the main body and the elongate member, that biases the elongate member in the rearward direction.

4. An intraocular lens insertion device as claimed in claim 3, wherein
the bias element comprises a spring.

5. An intraocular lens insertion device as claimed in claim 3, further comprising:
a lock that is configured to prevent reward movement of the elongate member in response to the first operating portion reaching the location at which the restraint prevents a finger from pushing the first operating portion forwardly.

6. An intraocular lens insertion device as claimed in claim 5, wherein
the lock comprises a projection on the first operating portion and a deflectable projection on the restraint.

7. An intraocular lens insertion device as claimed in claim 1, wherein
the restraint includes a slot; and
the slot and the first operating portion are configured such that the first operating portion can pass through the slot.

8. An intraocular lens insertion device as claimed in claim 1, further comprising:
a substantially u-shaped connector that connects the first operating portion to the second operating portion.

9. An intraocular lens insertion device as claimed in claim 1, wherein
the main body is configured to receive an intraocular lens cartridge.

10. An intraocular lens insertion device, comprising:

a main body having a lens advancement axis extending therethough and a main body stop surface;

a first plunger that is movable along the lens advancement axis in a forward direction and that includes a first plunger stop surface located such that the main body will prevent movement of the first plunger in the forward direction when the first plunger stop surface abuts the main body stop surface; and a second plunger that includes a lens contact portion and is movable along the lens advancement axis in a forward direction from an initial pre-use position to a fully extended position, the second plunger being operably connected to the first plunger such that movement of the first plunger in the forward direction results in movement of the second plunger in the forward direction and such that the second plunger is free to move in the forward direction relative to the first plunger;

wherein the respective locations of the main body stop surface and the first plunger stop surface are such that the second plunger will be located between the pre-use position and the fully extended position when the first plunger stop surface abuts the main body stop surface.

11. An intraocular lens insertion device as claimed in claim 10, wherein the main body defines a rearward end and the main body stop surface is associated with the rearward end of the main body; and the first plunger defines a rearward end and the first plunger stop surface is associated with the rearward end of the first plunger.

12. An intraocular lens insertion device as claimed in claim 10, wherein the main body defines a forward end and a rearward end and the main body stop surface is located between the forward end and the rearward end of the main body; and the first plunger defines a forward end and a rearward end and the first plunger stop surface is located between the forward end and the rearward end of the first plunger.

13. An intraocular lens insertion device as claimed in claim 12, wherein the main body includes a longitudinally extending slot that defines the main body stop surface; and the first plunger includes a pin, located within the longitudinally extending slot, that defines the first plunger stop surface.

14. An intraocular lens insertion device as claimed in claim 10, wherein the second plunger includes an engagement groove with a forward end; and the first plunger includes an engagement rib, located within the engagement groove, with a forward end that abuts the forward end of the engagement groove when the first plunger is moving in the forward direction.

15. An intraocular lens insertion device as claimed in claim 10, wherein the main body includes an integral lens placement portion, transition portion and nozzle.

16. An intraocular lens insertion device as claimed in claim 15, further comprising:

an intraocular lens stored in the lens placement portion.

* * * * *